(12) United States Patent
Berger et al.

(10) Patent No.: US 12,324,597 B2
(45) Date of Patent: Jun. 10, 2025

(54) METHODS AND SYSTEMS FOR ARTHROPLASTY

(71) Applicant: 3D-Side, Mont-Saint-Guibert (BE)

(72) Inventors: Jean-Marie Berger, Eden Prairie, MN (US); Laurent François René Paul, Mellery (BE); Khanh Tran Duy, Walhain (BE)

(73) Assignee: 3D-Side, Mont-Saint-Guibert (BE)

( * ) Notice: Subject to any disclaimer, the term of this patent is extended or adjusted under 35 U.S.C. 154(b) by 314 days.

(21) Appl. No.: 17/679,024

(22) Filed: Feb. 23, 2022

(65) Prior Publication Data

US 2022/0265289 A1  Aug. 25, 2022

Related U.S. Application Data

(60) Provisional application No. 63/152,732, filed on Feb. 23, 2021.

(51) Int. Cl.
  *A61B 17/17* (2006.01)
  *A61B 17/15* (2006.01)
  (Continued)

(52) U.S. Cl.
  CPC ........ *A61B 17/1775* (2016.11); *A61B 17/157* (2013.01); *A61F 2/30942* (2013.01); *A61B 2017/568* (2013.01); *A61B 2034/105* (2016.02)

(58) Field of Classification Search
  CPC .............. A61B 17/1775; A61B 17/157; A61B 2017/568; A61B 2034/105; A61F 2/30942
  See application file for complete search history.

(56) References Cited

U.S. PATENT DOCUMENTS

| | | |
|---|---|---|
| 9,561,111 B1 | 2/2017 | Goodman |
| 2005/0148843 A1 | 7/2005 | Roose |

(Continued)

FOREIGN PATENT DOCUMENTS

| | | |
|---|---|---|
| WO | WO 2015/052586 | 4/2015 |
| WO | WO 2020/239909 | 12/2020 |
| WO | WO 2020/255152 | 12/2020 |

OTHER PUBLICATIONS

"A Perspective Beyond: Vantage Ankle PSI," Exactech, 2021, 2 pages.

(Continued)

*Primary Examiner* — Sameh R Boles
(74) *Attorney, Agent, or Firm* — Sheridan Ross P.C.

(57) ABSTRACT

Devices and methods provided for joint arthroscopy contemplate and enable the provision of patient specific instruments (PSI). The devices and anatomical features of a patient are rendered adjustable by the provision of guide elements and feature to account for and enable repositioning of the anatomical features during surgery. Where the joint arthroscopy involves ankle arthroplasty, a PSI system includes a tibial PSI operable to be coupled to a tibia and a talar PSI operable to be coupled to a talus. Pins pass through the tibial PSI into the tibia and through the talar PSI into the talus. The tibia and talus are aligned based on the tibial PSI, the talar PSI, the pins, and optionally a connection guide operable to receive, or be coupled to, the pins. The tibial PSI and the talar PSI allow for the transfer of pre-operative planning to intra-operative procedures.

7 Claims, 22 Drawing Sheets

(51) Int. Cl.
*A61F 2/30* (2006.01)
*A61B 17/56* (2006.01)
*A61B 34/10* (2016.01)

(56) References Cited

U.S. PATENT DOCUMENTS

| | | |
|---|---|---|
| 2007/0179624 A1 | 8/2007 | Stone et al. |
| 2010/0262150 A1* | 10/2010 | Lian .................. A61B 17/15 |
| | | 606/103 |
| 2016/0256293 A1* | 9/2016 | Mauldin ............... A61F 2/4606 |
| 2018/0177513 A1* | 6/2018 | Stemniski ............. A61B 17/15 |
| 2018/0296356 A1 | 10/2018 | Sbaiz et al. |
| 2019/0133691 A1 | 5/2019 | Iannotti et al. |

OTHER PUBLICATIONS

"Prophecy," Total Ankle Institute, 2019, retrieved Feb. 23, 2021 from https://www.totalankleinstitute.com/infinity-products/prophecy-preoperative-navigation-guides/, 7 pages.

Invitation to Pay Additional Fees for International (PCT) Patent Application No. PCT/US2022/49605, dated Feb. 3, 2023, 3 pages.

International Search Report and Written Opinion for International (PCT) Patent Application No. PCT/US2022/049605, dated Apr. 5, 2023, 17 pages.

International Preliminary Report on Patentability for International (PCT) Patent Application No. PCT/US2022/049605, dated May 23, 2024, 10 pages.

\* cited by examiner

METHODS AND SYSTEMS FOR ARTHROPLASTY

CROSS-REFERENCE TO RELATED APPLICATIONS

This U.S. Non-Provisional Patent Application claims the benefit of priority of U.S. Provisional Patent Application Ser. No. 63/152,732, filed Feb. 23, 2021, the entire disclosure of which is hereby incorporated by reference.

FIELD OF THE DISCLOSURE

The present disclosure generally relates to orthopedic surgery. Various embodiments of the present disclosure relate generally to methods and systems for ankle surgery. In some embodiments, methods and systems related to Patient-Specific Instruments (hereafter "PSI" or "PSIs") for use during total ankle arthroplasty (joint replacement) are provided.

BACKGROUND

A human ankle joint includes the tibia, fibula, and talus. Where a patient's natural bone is not preservable (e.g., between the tibia and the talus), ankle arthroplasty (or ankle joint replacement) involves the removal of damaged portions and replacing with new prostheses (artificial components).

Installing the prostheses during surgery requires precise and accurate positioning to reduce or prevent possible misalignment or mispositioning. Although preoperative planning may take into consideration known or natural medical configurations, the local anatomy of a patient may have deviations which may not be observed until during surgery. During preoperative planning, virtual planning using a software may be performed by the surgeon to correct an abnormal anatomy. Patient Specific Instruments (PSI) provide the ability to transpose the virtual planning into the operative room and perform procedures on a real patient. For example, PSIs are used in orthopedic applications for guiding instruments such as saw blades or pins to perform cutting, reaming, drilling, fixing bones, or positioning (parts of) implants or protheses.

One existing PSI system available for total ankle arthroplasty includes the Prophecy system from STRYKER™ to guide the Infinity total ankle implant. The PSIs are positioned on their respective bones (e.g., tibia and talus) and guide pins or screws into a bone. The pins are used to slide a metallic reusable cutting guide to perform the bone cutting.

Another existing PSI system available for total ankle arthroplasty includes the Vantage PSI from Exactech/3D System to guide the Vantage total ankle implant. The tibial PSI is attached to the tibia using pins. A saw blade is guided during the bone cutting. Then a talar PSI is provided over the 2 pins, fitting on the talus bone. The talus is then brought in its final position. Finally, the cutting is done through a slot or channel provided in the PSI.

A major concern related to total ankle implant positioning and arthroplasty is the ability (or inability) to control the transversal rotation and antero-posterior position of implants. The two above-mentioned existing PSI systems aim to replicate the position of bones as they have been virtually planned by the software. However, there is no guarantee that those positions will be reachable or desirable during the surgery on the real patient. In some cases, the talus bone cannot be positioned as planned because of ligament or soft tissues tension. This is especially true for the antero-posterior position (e.g., as depicted in FIG. 1) and/or the transverse rotation (e.g., as depicted in FIG. 2). of the talar bone (or talus 4) relative to the tibial bone (or tibia 2).

The above-mentioned existing PSI systems rely on a single type of landmark (or landmarks), such as the periphery of the bone, surface of the bone, or landmark external to the joint. As a result, they do not always fit properly on the bone when the landmarks are difficult to expose, very damaged, or are generally abnormal. In addition, the above-mentioned existing PSI systems do not provide intra-operative feedback on the correctness of bone positions during surgery. In the case the talus cannot be positioned as planned, there are limited options for surgeons. For example, surgeons in this situation are presented with the option of (1) proceeding with the existing PSI or (2) continuing manually without using the PSI. Both options pose risks.

Accordingly, there has been a long-felt and unmet need to provide methods and systems for PSIs that allow for flexibility during arthroplasty operations.

SUMMARY

Embodiments of the present disclosure include improved systems and methods for arthroplasty. In embodiments, the systems and method for arthroplasty include PSI which are mapped to a particular patient, such that observed abnormalities of the anatomy of the patient may be taken into consideration. In addition, the PSI of the present disclosure should allow for flexibility during arthroplasty, where additional or increased abnormalities of the anatomy of the patient are observed during the operation.

In various embodiments, a tibial PSI is provided to guide either a saw blade for cutting a bony structure or a direction for instrument or implant positioning. In additional embodiments, a talar PSI is provided to guide a bone cutting or direction for instrument or implant positioning. In further embodiments, a connection guide is provided to guide the drilling of pins into the bone.

In various embodiments, PSI methods and systems of the present disclosure provide the ability to assess intra-operatively if the planned talus position is realistic and desired. In addition, PSI methods and systems of the present disclosure provide the ability to allow a surgeon to adapt a procedure and device(s) to fit with the new bone position chosen by the surgeon, when the surgeon decides intra-operatively that the position is not optimal for a specific patient. Further, PSI methods and systems of the present disclosure provide the ability to provide a marker reference for usage of Augmented Reality (AR) glasses for intra-operative navigation. The flexibility provided by embodiments of the present disclosure allows a surgeon to address any challenges linked to deformed anatomy or soft tissue tensioning that cannot always be seen on a computed (or computerized) tomography (CT) scan and therefore is not always anticipated during the planning or pre-operative phase.

In one particular embodiment, a patient-specific instrument (PSI) includes a tibial PSI with at least one tibial PSI surface contoured to conform to at least one tibial contact surface of a tibia. The contouring of the at least one tibial PSI surface is operable to provide an indication of a mispositioning of the tibial PSI on the tibia. The tibial PSI includes at least one tibial aperture operable to receive at least a first pin. The at least one tibial aperture corresponds to a pre-determined placement of the at least a first pin within the tibia. The tibial PSI is couplable to the tibia via the at least a first pin. The talar PSI with at least one talar PSI surface contoured to conform to at least one talar contact surface of a talus. The contouring of the at least one talar PSI surface is operable to provide an indication of a mispositioning of the talar PSI on the talus. The talar PSI includes at least one talar aperture operable to receive at least a second pin. The at least one talar aperture corresponds to a pre-determined placement of the at least a second pin within the talus. The talar PSI is couplable to the talus via the at least a second pin.

In embodiments, at least one of the placement of the at least a first pin within the tibia or the placement of the at least a second pin within the talus is pre-determined during at least one virtual pre-operative planning. In embodiments, at least one of the tibial PSI is designed from a scan of the tibia during the at least one virtual pre-operative planning, or the talar PSI is designed from a scan of the talus during the at least one virtual pre-operative planning.

In embodiments, the PSI system includes a connection guide configured to align at least one of the tibia or the talus during intra-operative procedures. The connection guide is operable to at least one of receive the at least a first pin coupling the tibial PSI to the tibia, or receive the at least a second pin coupling the talar PSI to the talus. In embodiments, at least one of the tibial PSI, the talar PSI, or the connection guide is fabricated via at least one additive manufacturing process.

In embodiments, the at least a first pin includes at least one distal pin and at least one proximal pin. The at least one tibial aperture includes at least one distal drilling aperture corresponding to a pre-determined placement of the at least one distil pin within the tibia and at least one proximal drilling aperture corresponding to a pre-determined placement of the at least one proximal pin within the tibia. In embodiments, the at least a second pin includes at least one alignment pin. The at least one talar aperture includes at least one alignment aperture corresponding to a pre-determined placement of the at least one alignment pin within the talus.

In embodiments, the tibial PSI includes at least one cutting guide operable to receive a cutting device for producing at least one resected surface on the tibia. In embodiments, the talus includes a talar PSI exterior surface operable to be aligned with an exterior surface of the tibia, and a talar PSI gap surface operable to be aligned with the at least one resected surface of the tibia.

In embodiments, at least one of the tibial PSI or the talar PSI includes one or more of a guide aperture for inserting a protective guide, or a cleaning aperture for removing excess manufacturing material or cleaning material. In embodiments, the talar PSI includes a handle for adjustment of the talar PSI relative to the talus.

In another particular embodiment, a method for aligning a tibia and talus during ankle arthroplasty may include, but is not limited to, positioning a tibial Patient-Specific Instrument (PSI) on a tibia. The tibial PSI includes at least one tibial PSI surface contoured to conform to at least one tibial contact surface of the tibia. The contouring of the at least one tibial PSI surface is operable to provide an indication of a mispositioning of the tibial PSI on the tibia. The method may include, but is not limited to, drilling the tibia via at least one distal drilling aperture in the tibial PSI. The method may include, but is not limited to, inserting at least one distil pin in the tibia. The at least one distal drilling aperture corresponds to a pre-determined placement of the at least one distil pin within the tibia. The method may include, but is not limited to, resecting a portion of the tibia using at least one cutting guide on the tibial PSI to form a resected tibia surface. The method may include, but is not limited to, positioning a talar PSI on a talus. The talar PSI includes at least one talar PSI surface contoured to conform to at least one talar contact surface of the talus. The contouring of the at least one talar PSI surface is operable to provide an indication of a mispositioning of the talar PSI on the talus. The method may include, but is not limited to, drilling the talus via at least one alignment drilling aperture in the talar PSI. The method may include, but is not limited to, inserting at least one alignment pin in the talus. The at least one alignment drilling aperture corresponds to a pre-determined placement of the at least one alignment pin within the talus. The method may include, but is not limited to, adjusting the talar PSI and the talus relative to the tibia with the at least one alignment pin inserted in the talus to be consistent with pre-determined positions. The method may include, but is not limited to, drilling the tibia via at least one proximal drilling aperture in the tibial PSI. The method may include, but is not limited to, inserting at least one proximal pin in the tibia. The at least one proximal drilling aperture corresponds to a pre-determined placement of the at least one proximal pin within the tibia.

In embodiments, the pre-determined positions for the talar PSI and the talus is determined during virtual pre-operative planning. In embodiments, the adjusting the talar PSI includes aligning a talar PSI exterior surface to an exterior surface of the tibia, and aligning a talar PSI gap surface to the resected surface of the tibia.

In embodiments, the method may include, but is not limited to, removing at least one additional contact from an upper portion of the tibial PSI by cutting at least one connector coupling the at least one additional contact to the upper portion prior to resecting the tibia. The at least one additional contact is operable to provide an indication of the mispositioning of the tibial PSI on the tibia prior to being removed.

In embodiments, the method may include, but is not limited to, attaching a connection guide to one or more of the at least one proximal pin and the at least one alignment pin. In embodiments, the method may include, but is not limited to, removing the tibial PSI from the tibia after resecting the portion of the tibia and prior to positioning the talar PSI on the talus. In embodiments, the method may include, but is not limited to, re-positioning the tibial PSI on the tibia after adjusting the talar PSI and the talus and prior to drilling the at least one proximal drilling aperture. In embodiments, the method may include, but is not limited to, removing the tibial PSI from the tibia after drilling the at least one proximal drilling aperture and prior to inserting the at least one proximal pin. In embodiments, the method may include, but is not limited to, removing the connection guide and the talar PSI after aligning the tibia and the talus based on the placement of at least one proximal pin and the placement of the at least one alignment pin.

In another particular embodiment, a method for ankle arthroplasty may include, but is not limited to, evaluating relative positions of a tibia and a talus during pre-operative planning. The method may include, but is not limited to, providing a patient-specific instrument (PSI) system including a tibial PSI designed based on the tibia and a talar PSI designed based on the talus, during the pre-operative planning. The method may include, but is not limited to, comparing the position of the tibia and talus based on the relative positions of the tibia and the talus evaluated during the pre-operative planning, and observed positions of the tibia and the talus during the intra-operative procedure during an intra-operative procedure. The method may include, but is not limited to, coupling the tibial PSI to the tibia and the talar PSI on the talus during the intra-operative procedure. The method may include, but is not limited to, adjusting at least one of the tibia via the tibial PSI or the talus via the talar PSI during the intra-operative procedure. The method may include, but is not limited to, removing the tibial PSI and the talar PSI during the intra-operative procedure.

In embodiments, the method may include, but is not limited to, installing a first pin in the tibia via the tibial PSI during the inter-operative procedure. The method may include, but is not limited to, installing a second pin in the talus via the talar PSI during the inter-operative procedure. The method may include, but is not limited to, aligning the tibia and the talus via the first pin, the second pin, and a connection guide coupled to the first pin and the second pin during the inter-operative procedure.

In embodiments, the method may include, but is not limited to, designing the tibial PSI from a scan of the tibia during the pre-operative planning. The method may include, but is not limited to, designing the talar PSI from a scan of the talus during the pre-operative planning. The method may include, but is not limited to, designing a flexible bone model from the scan of the tibia and the scan of the talus during the pre-operative planning. The flexible bone model includes a select range of articulation. The flexible bone model is operable to receive the tibial PSI and the talar PSI. The flexible bone model is operable to test the tibial PSI relative to the tibia and the talar PSI relative to the talus during simulated repositioning.

Additional embodiments are contemplated by the present disclosure which include a PSI system including a single PSI which is operable to couple to the tibia and/or the talus separately or simultaneously. Additional embodiments are contemplated by the present disclosure which include PSI (and/or a PSI system) being designed for and usable during for any type of arthroplasty.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

The term "a" or "an" entity, as used herein, refers to one or more of that entity. As such, the terms "a" (or "an"), "one or more" and "at least one" can be used interchangeably herein.

The transitional term "comprising" is synonymous with "including," "containing," or "characterized by," is inclusive or open-ended and does not exclude additional, unrecited elements or method steps.

Unless otherwise indicated, all numbers expressing quantities, dimensions, conditions, ratios, ranges, and so forth used in the specification and claims are to be understood as being modified in all instances by the term "about" or "approximately". Accordingly, unless otherwise indicated, all numbers expressing quantities, dimensions, conditions, ratios, ranges, and so forth used in the specification and claims may be increased or decreased by approximately 5% to achieve satisfactory results. Additionally, where the meaning of the terms "about" or "approximately" as used herein would not otherwise be apparent to one of ordinary skill in the art, the terms "about" and "approximately" should be interpreted as meaning within plus or minus 5% of the stated value.

All ranges described herein may be reduced to any sub-range or portion of the range, or to any value within the range without deviating from the invention. For example, the range "5 to 55" includes, but is not limited to, the sub-ranges "5 to 20" as well as "17 to 54."

The transitional phrase "consisting of" excludes any element, step, or ingredient not specified in the claim, but does not exclude additional components or steps that are unrelated to the disclosure such as impurities ordinarily associated therewith.

The transitional phrase "consisting essentially of" limits the scope of a claim to the specified materials or steps and those that do not materially affect the basic and novel characteristic(s) of the claimed invention.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

The preceding is a simplified summary of the disclosure intended to provide an understanding of some aspects of the settler devices of this disclosure. This Summary is neither an extensive nor exhaustive overview of the invention and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. As will be appreciated, other embodiments are possible using, alone or in combination, one or more of the features set forth above or described herein. For example, it is contemplated that various features and devices shown and/or described with respect to one embodiment may be combined with or substituted for features or devices of other embodiments regardless of whether or not such a combination or substitution is specifically shown or described herein. Additional aspects of the present invention will become more readily apparent from the Detailed Description, particularly when taken together with the drawings.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

Figure 2:
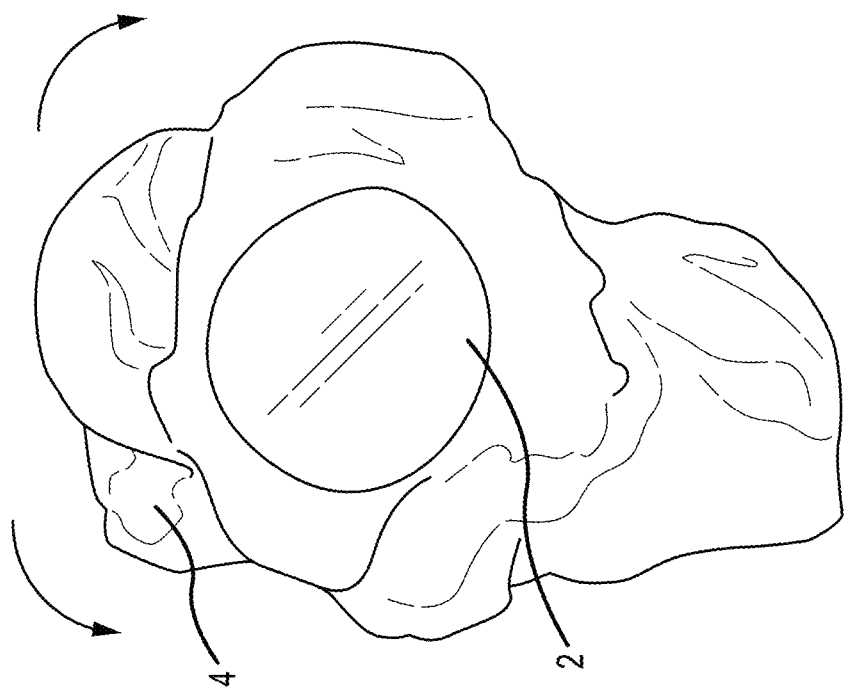
Figure 1:
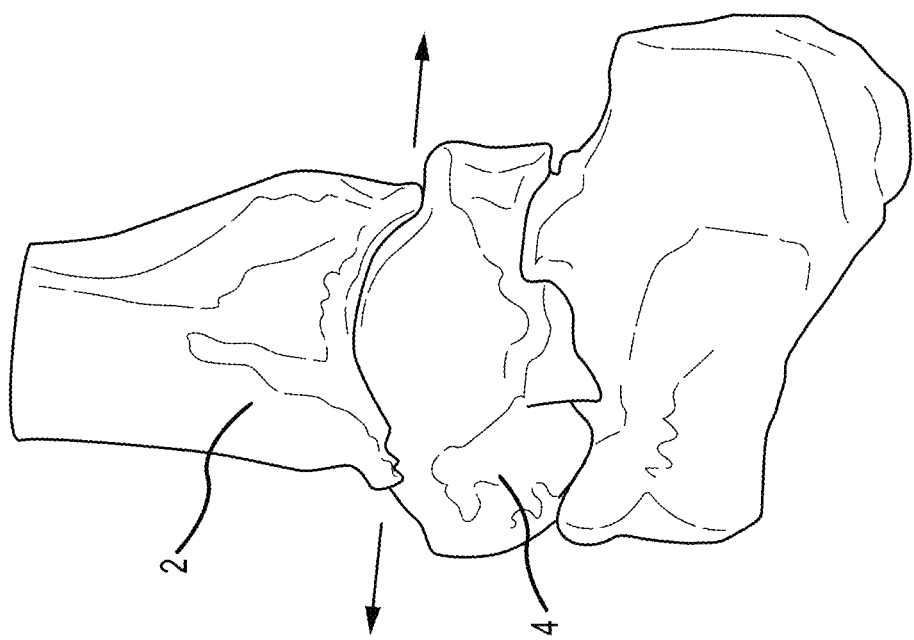
Figure 4:
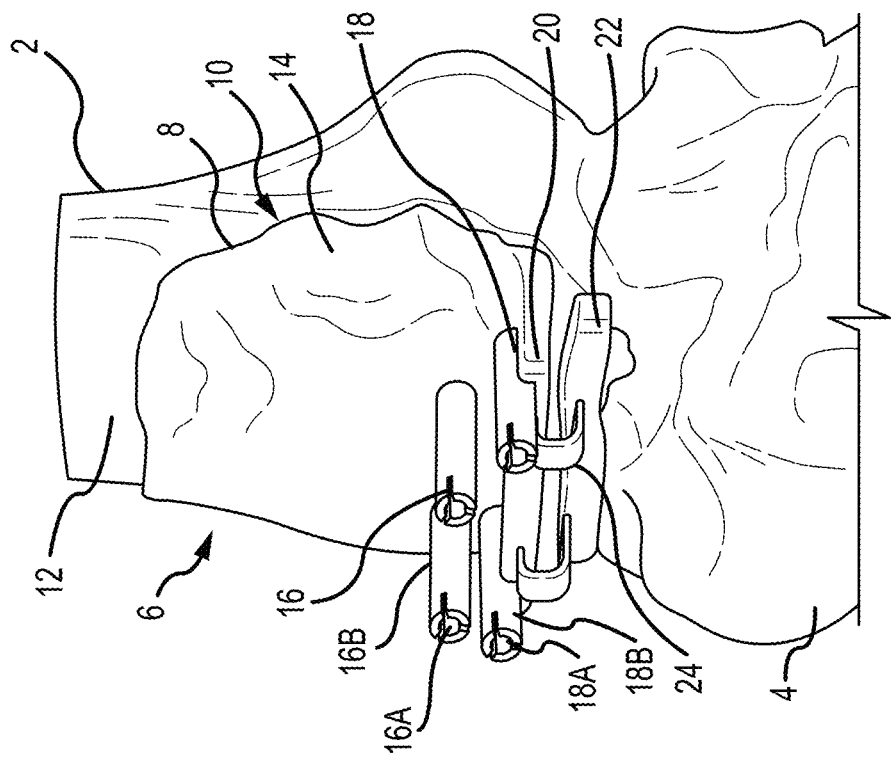
Figure 3:
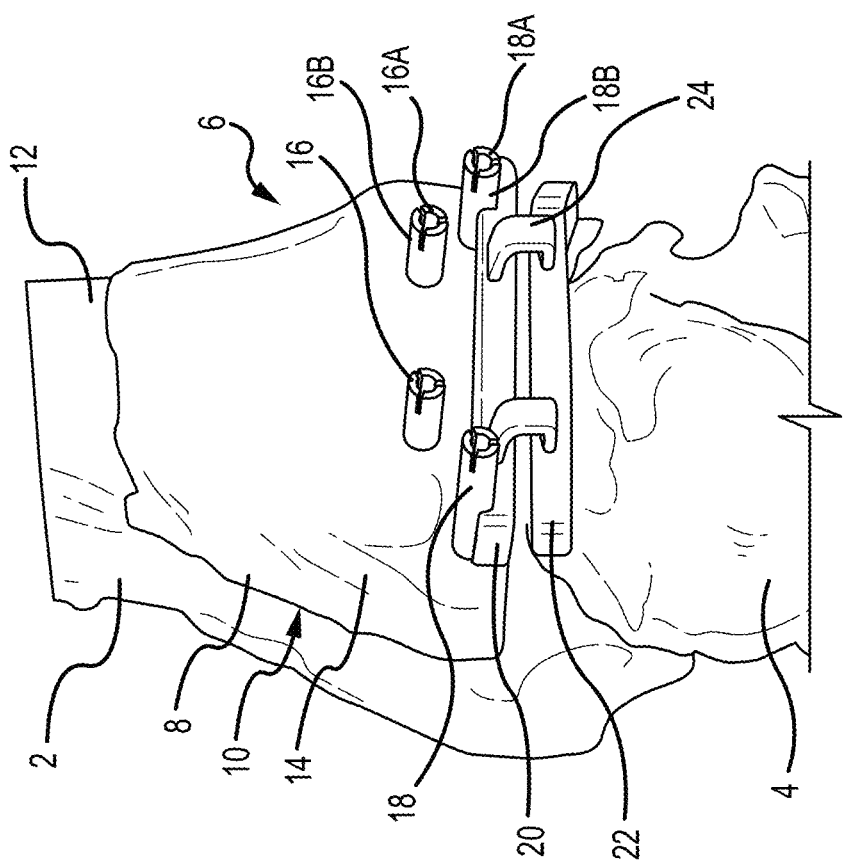
Figure 5:
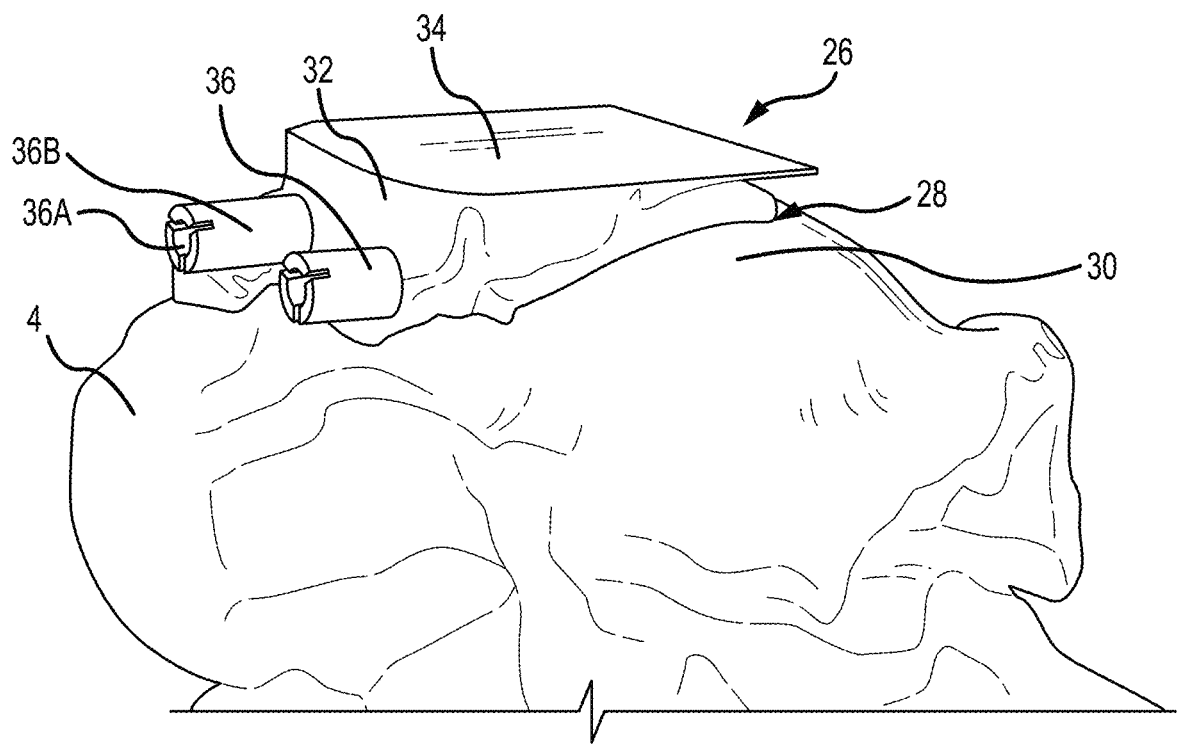
Figure 6:
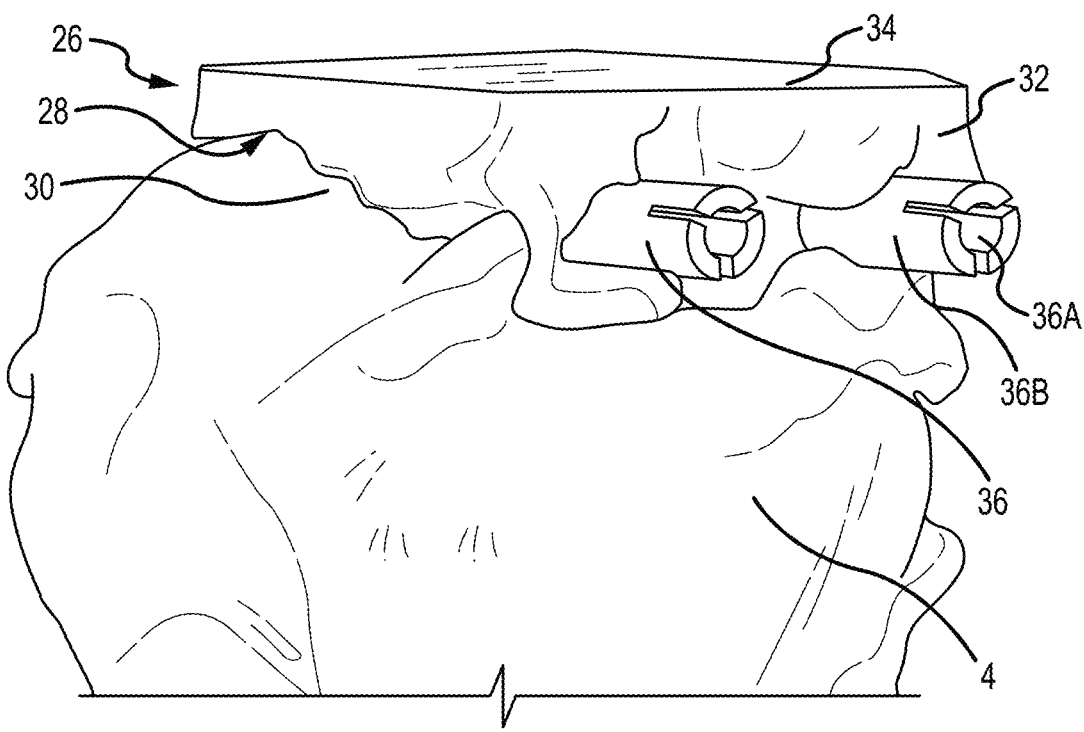
Figure 7:
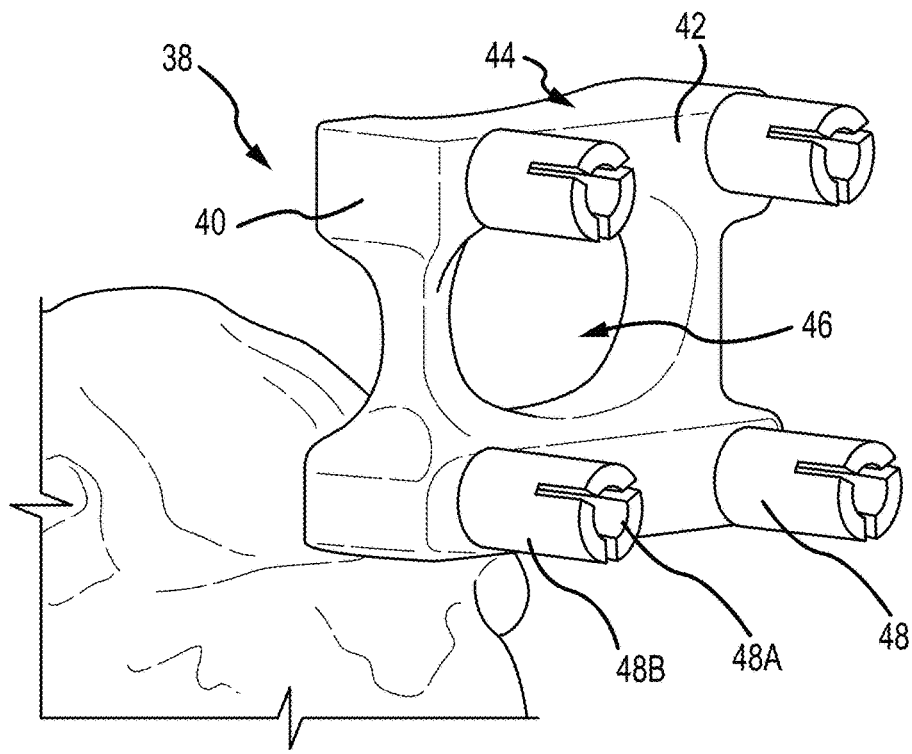
Figure 8:
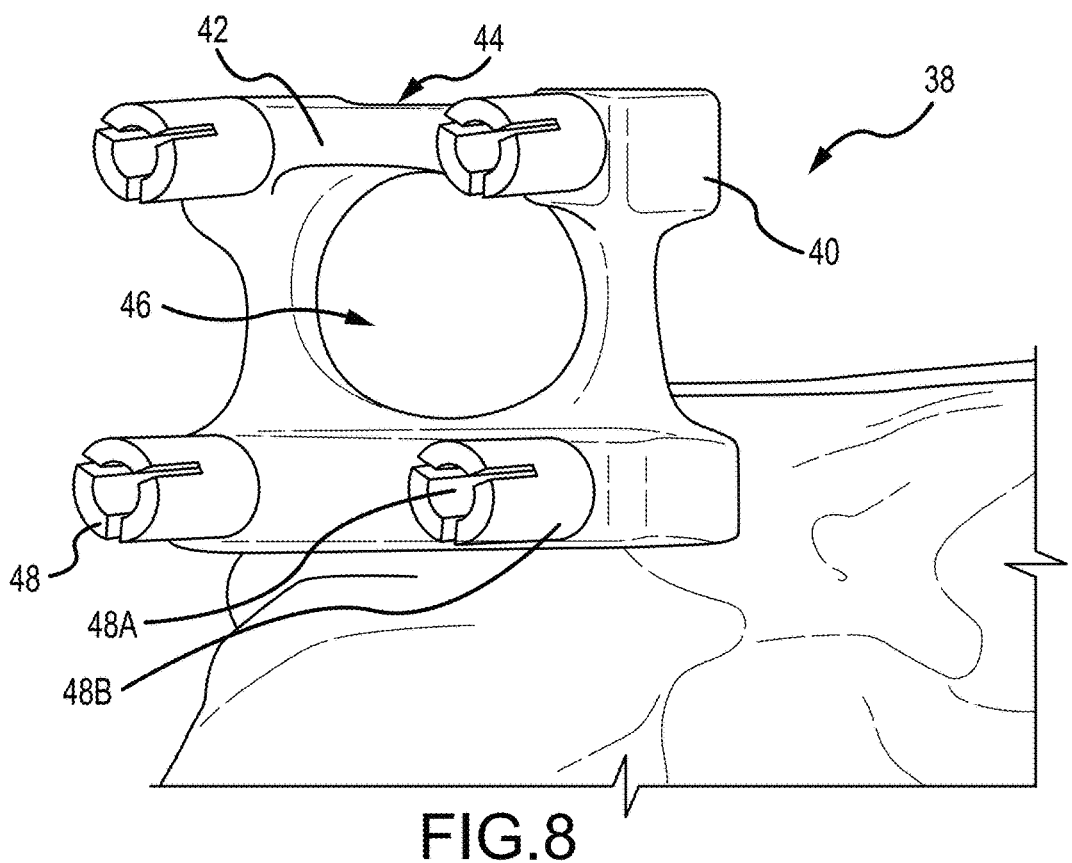
Figure 10:
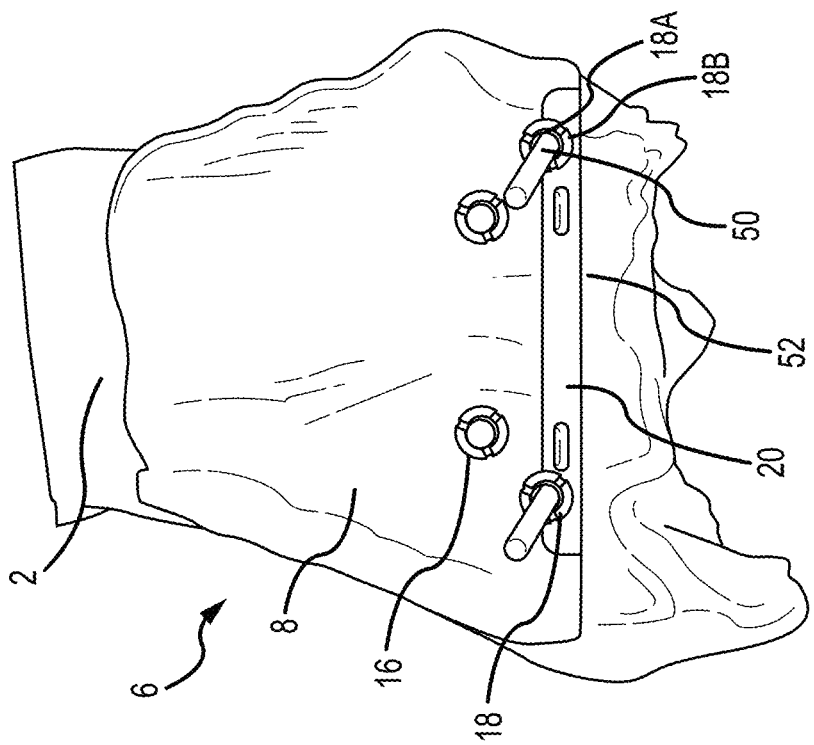
Figure 9:
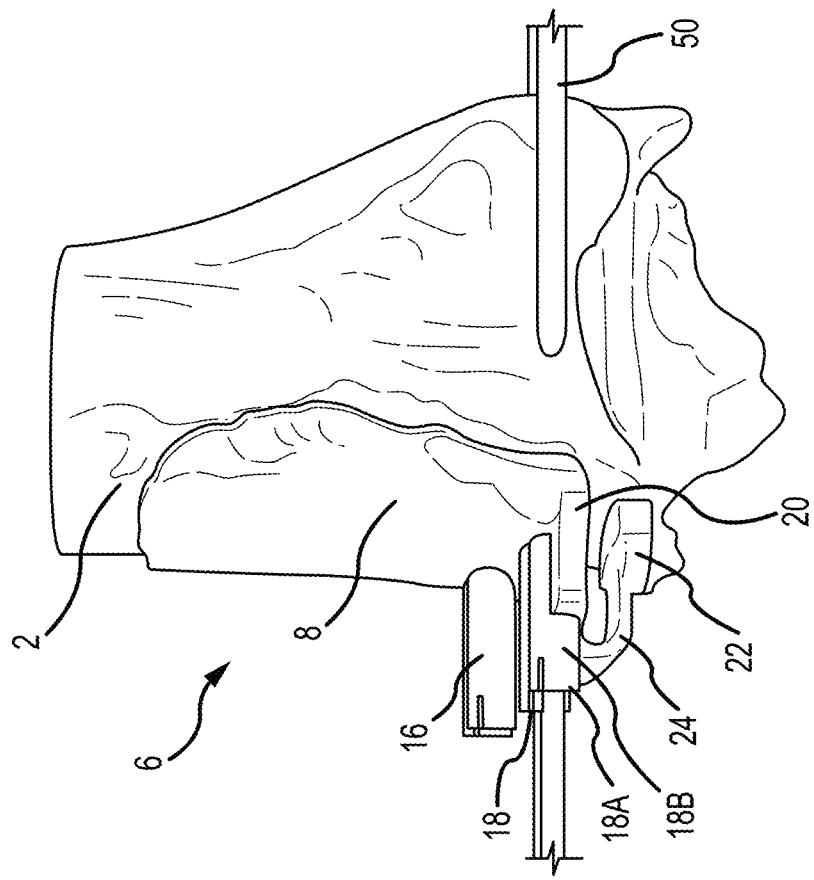
Figure 12:
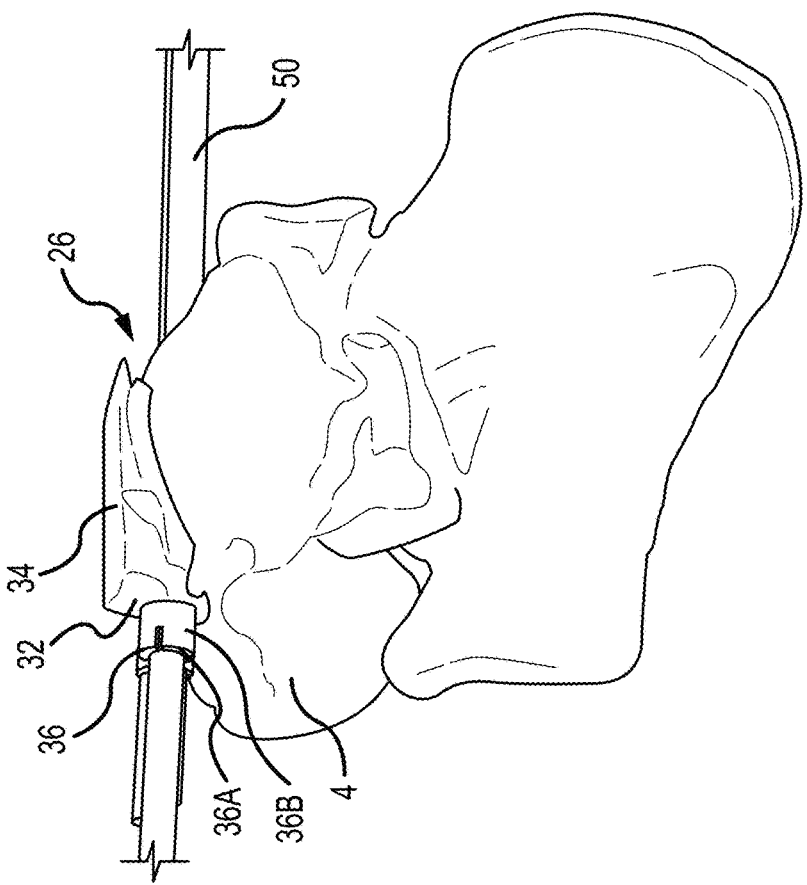
Figure 11:
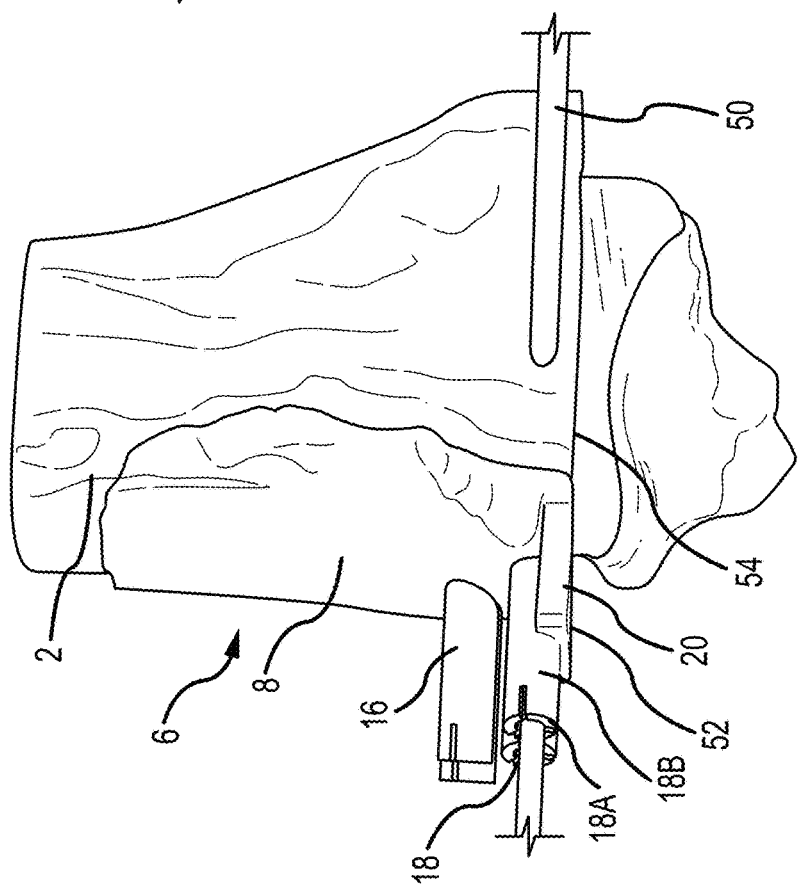
Figure 14:
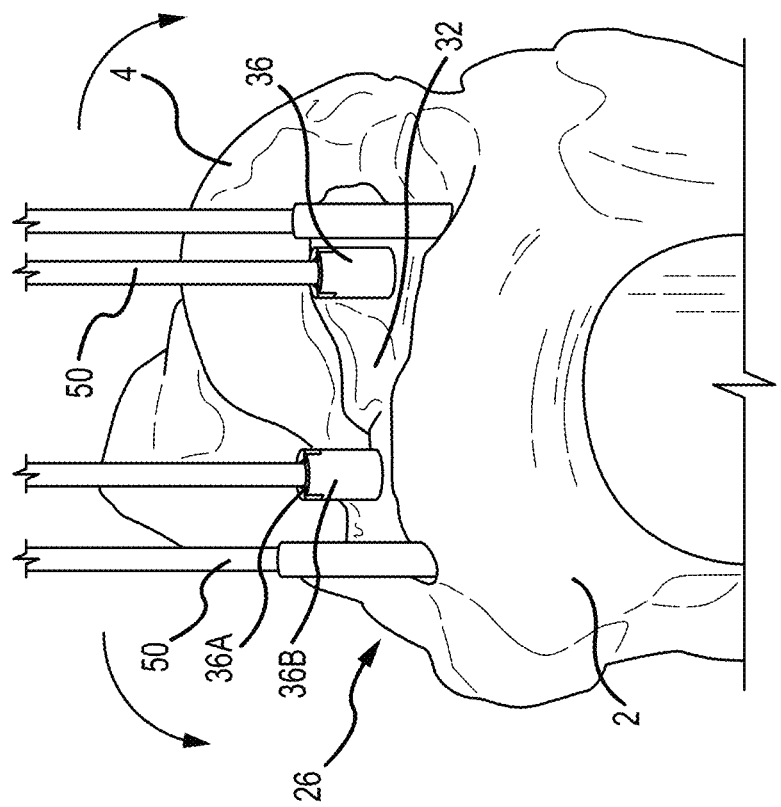
Figure 13:
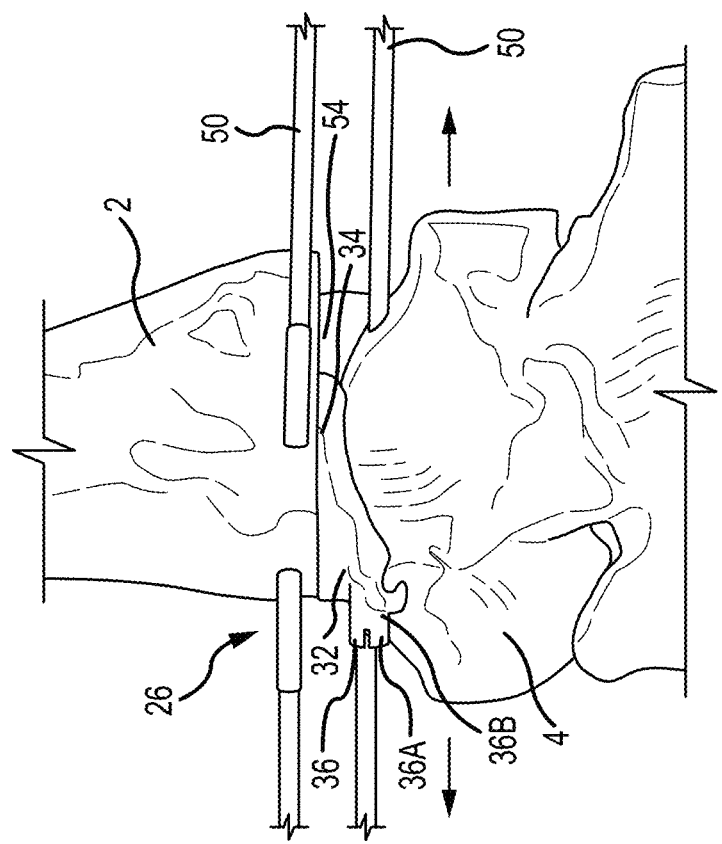
Figure 16:
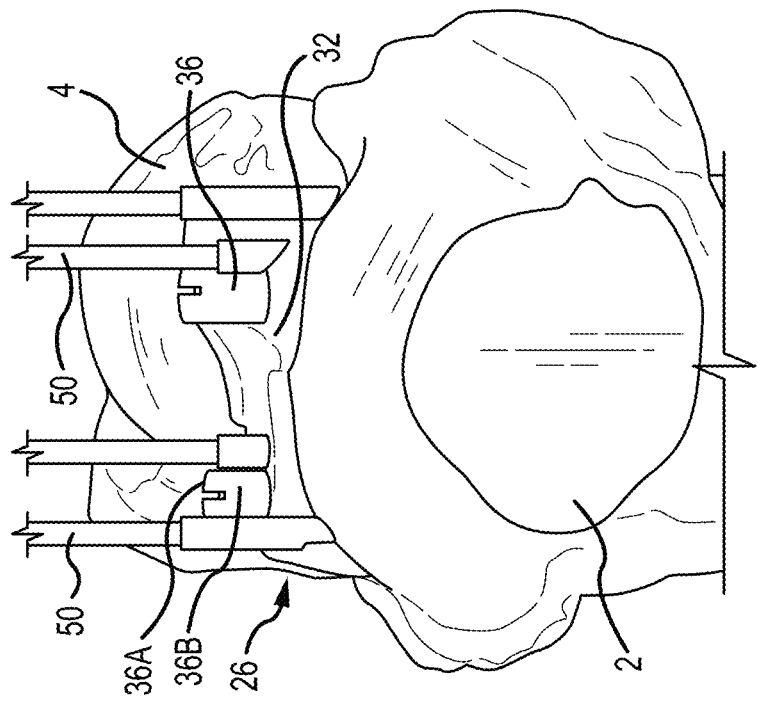
Figure 15:
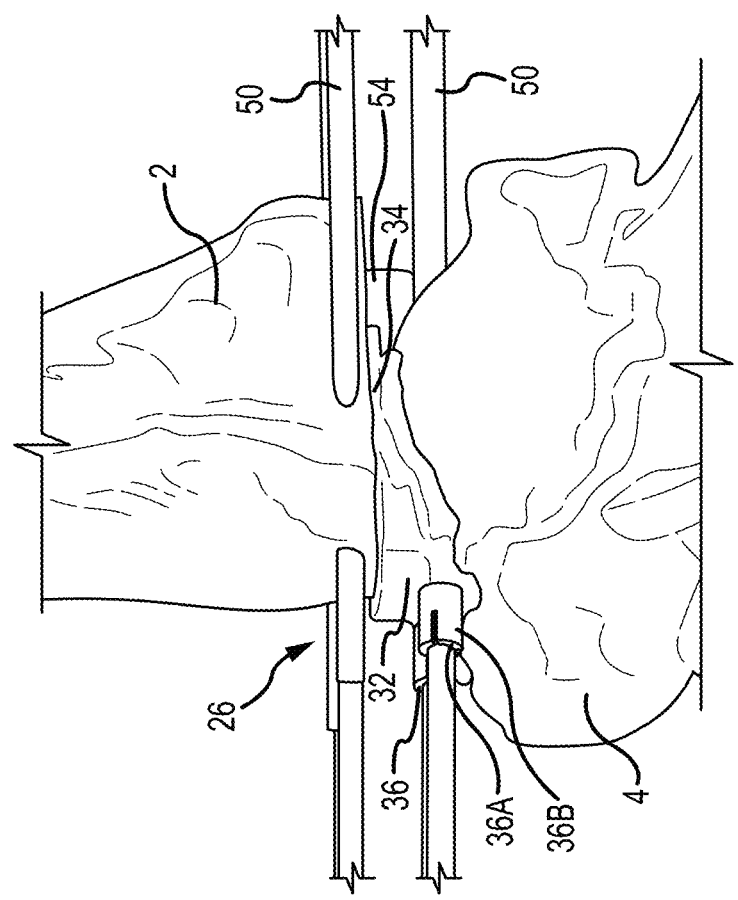
Figure 18:
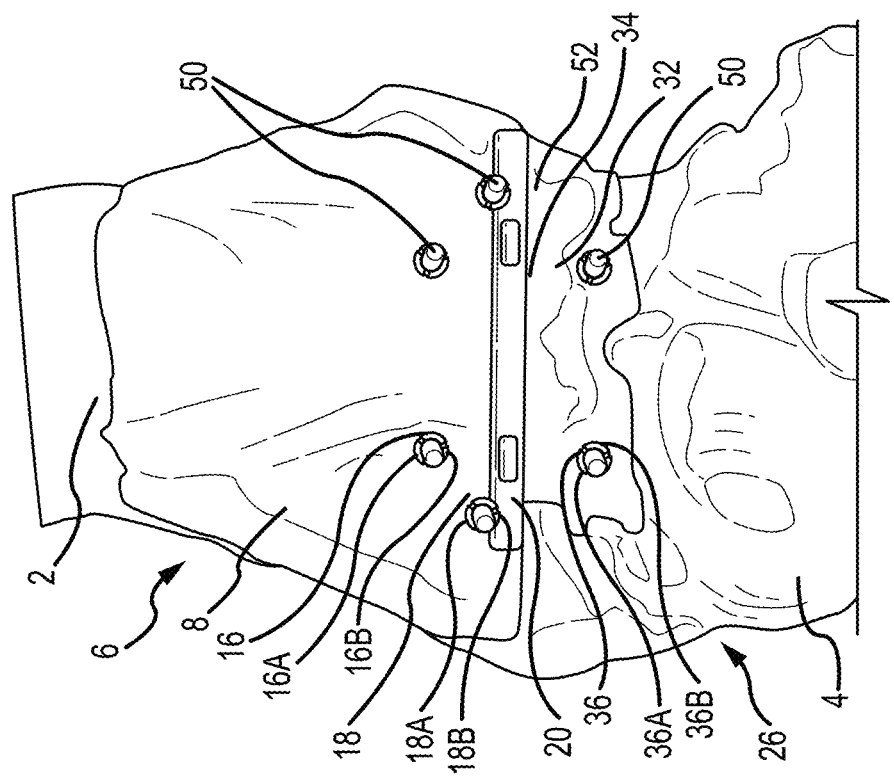
Figure 17:
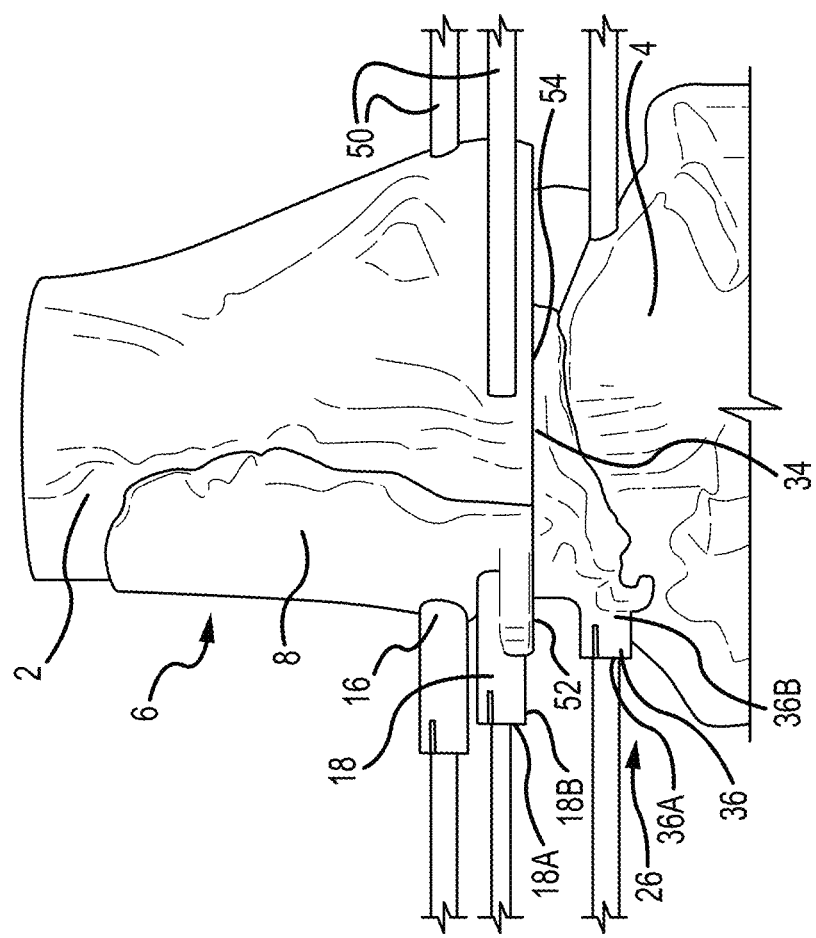
Figure 19:
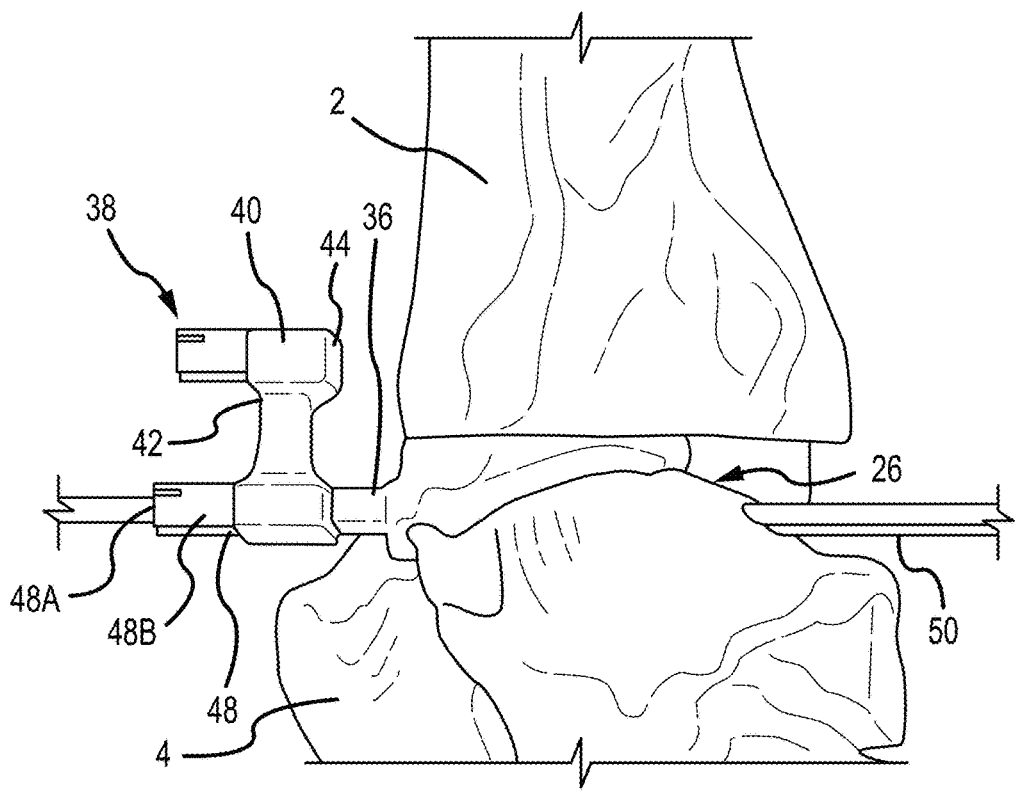
Figure 20:
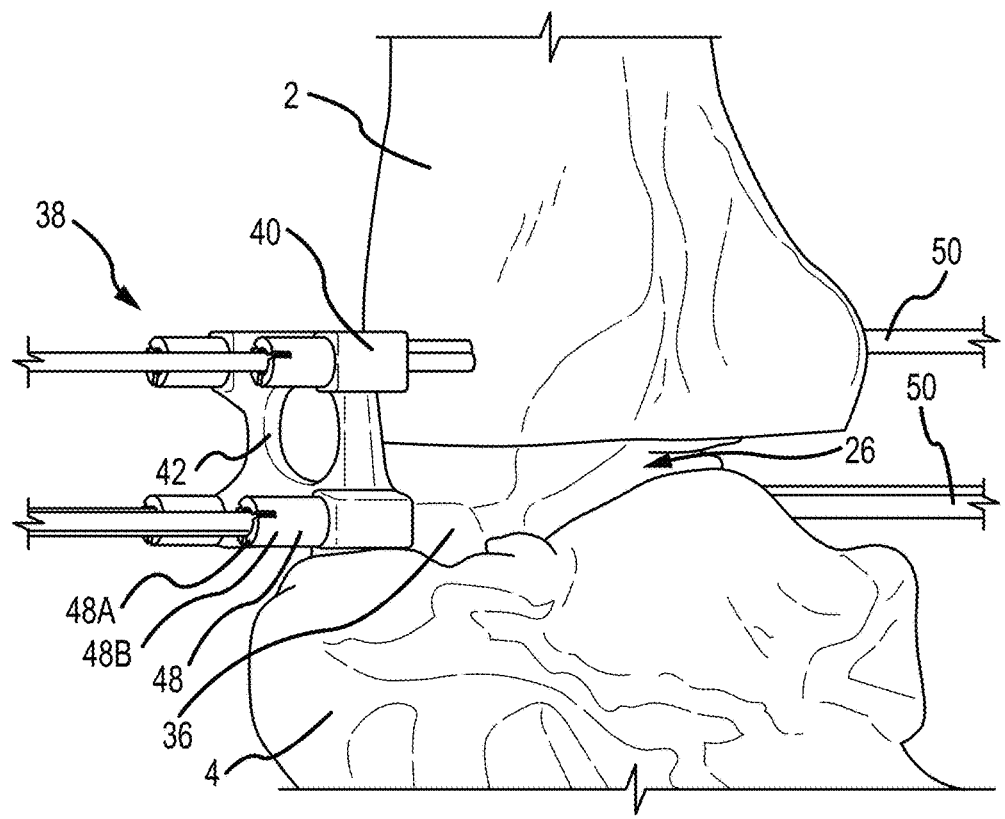
Figure 21:
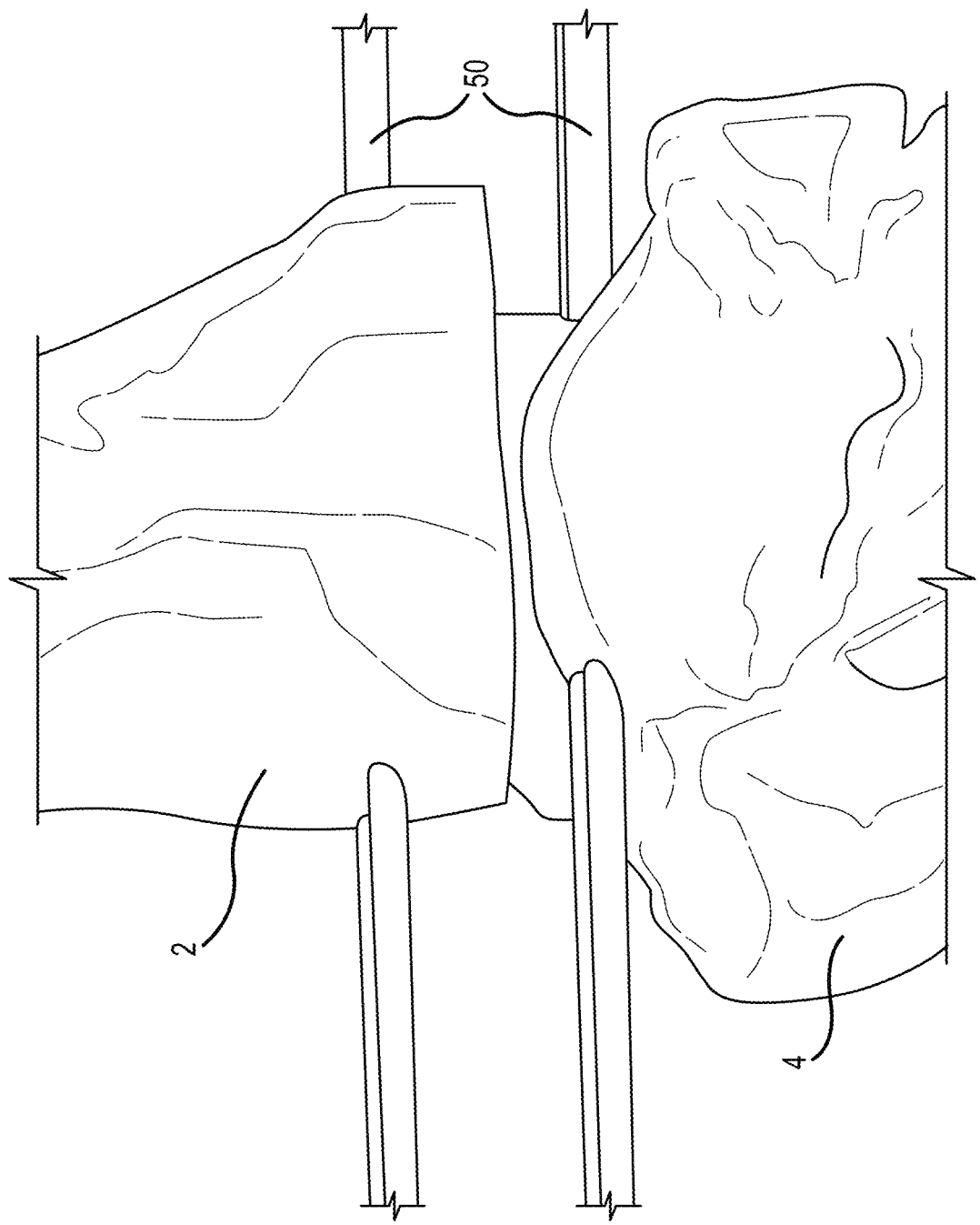
Figure 22:
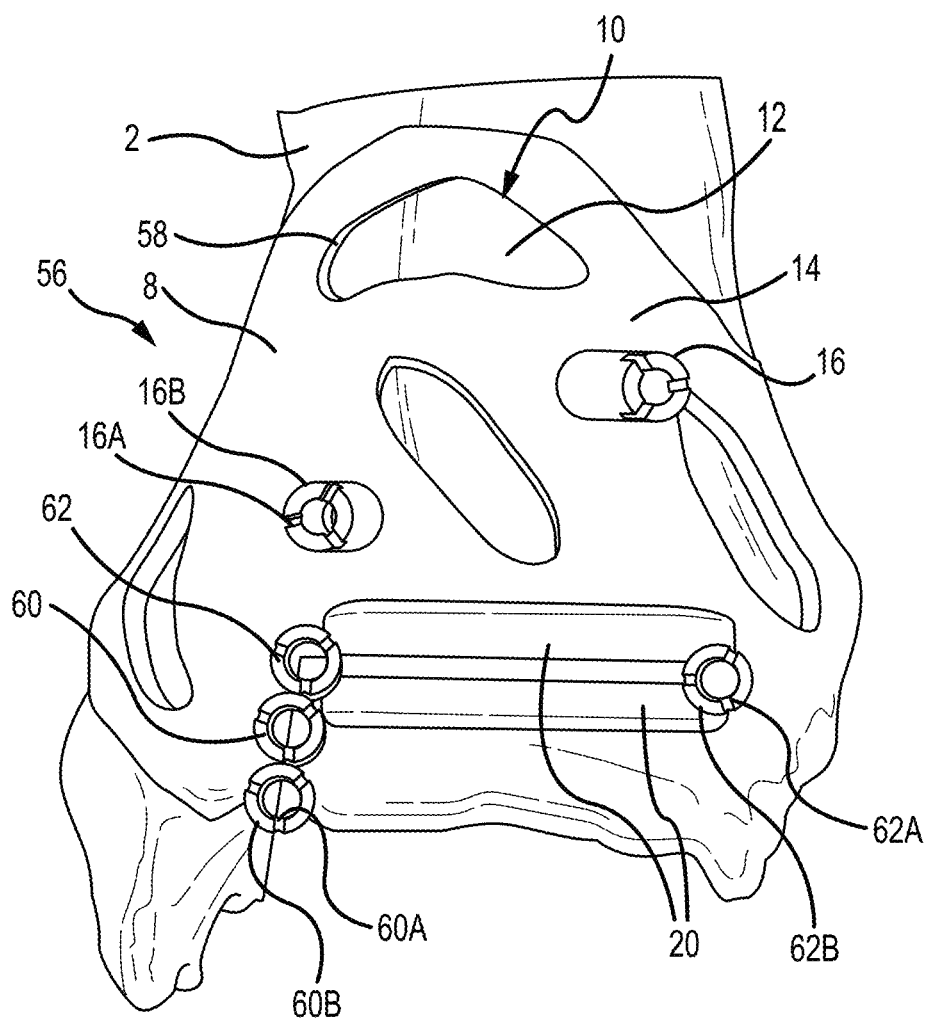
Figure 24:
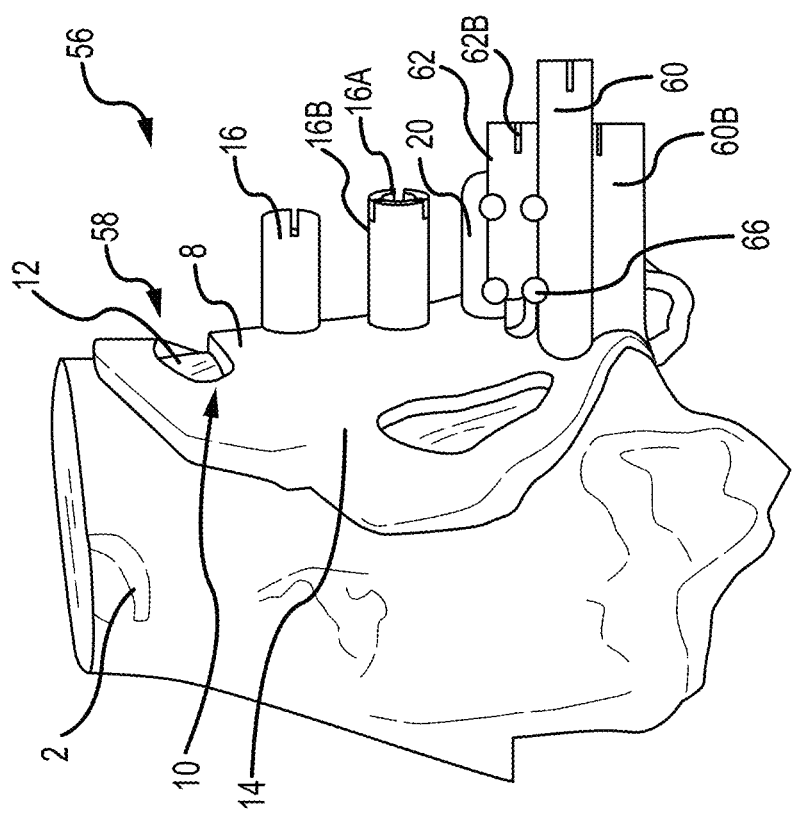
Figure 23:
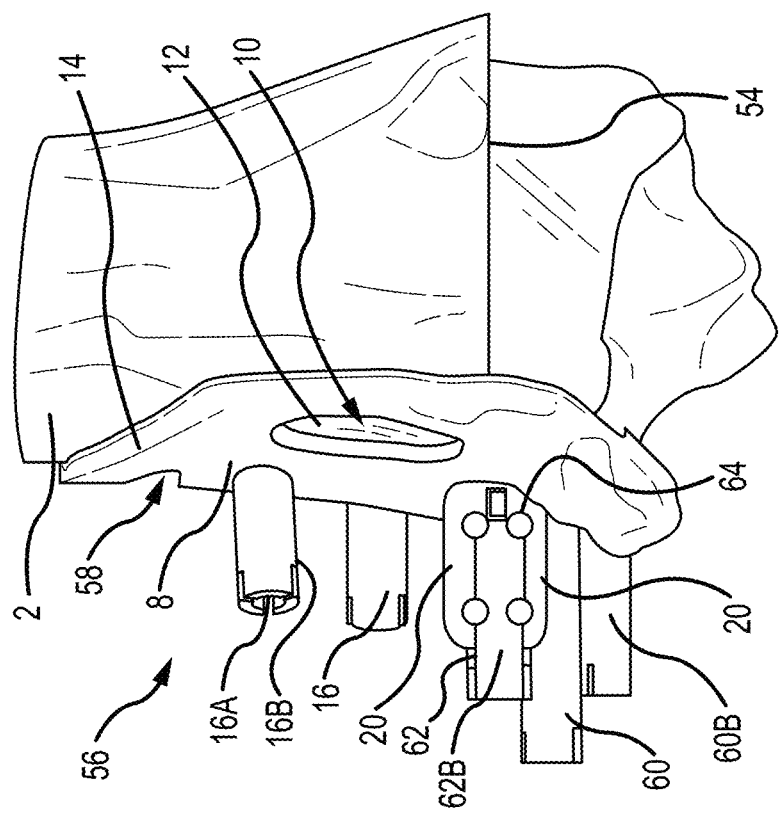
Figure 25:
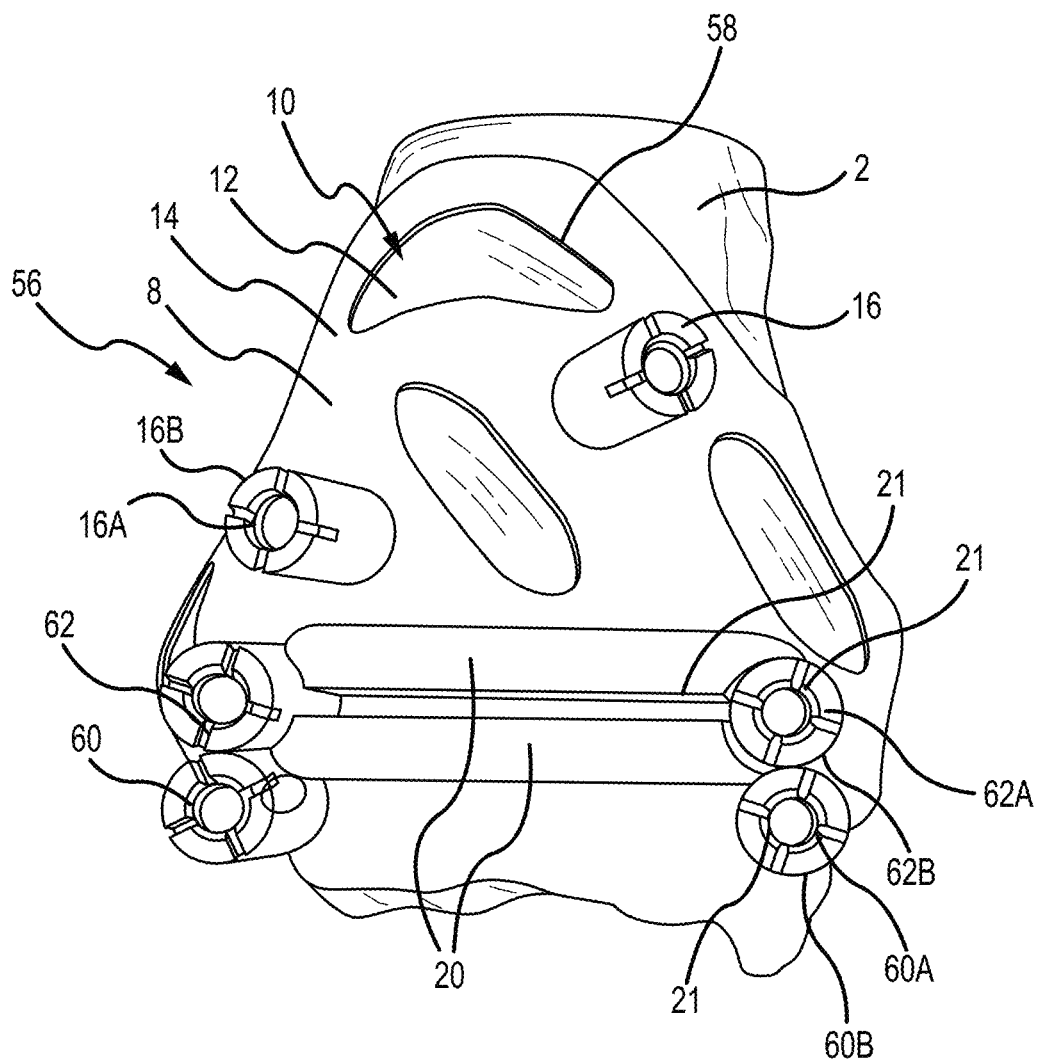
Figure 26:
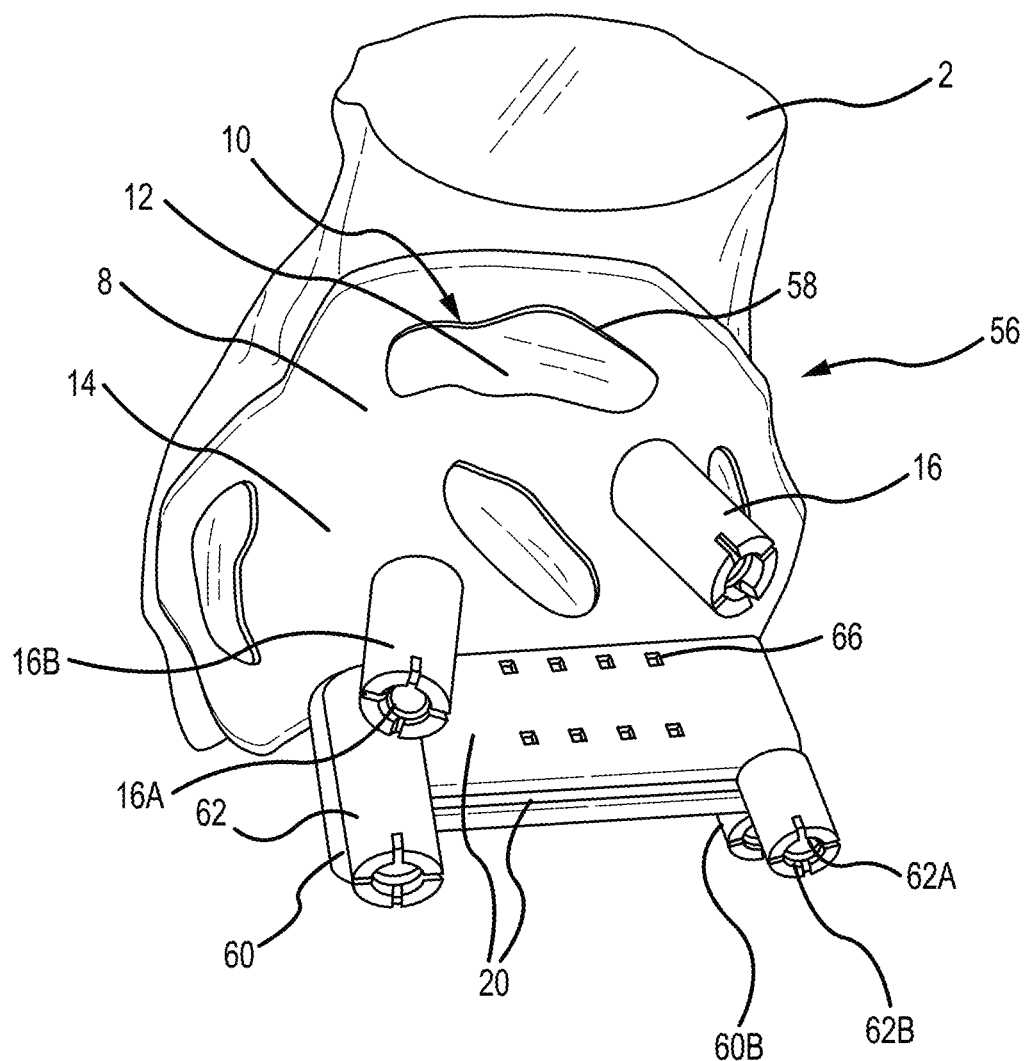
Figure 27:
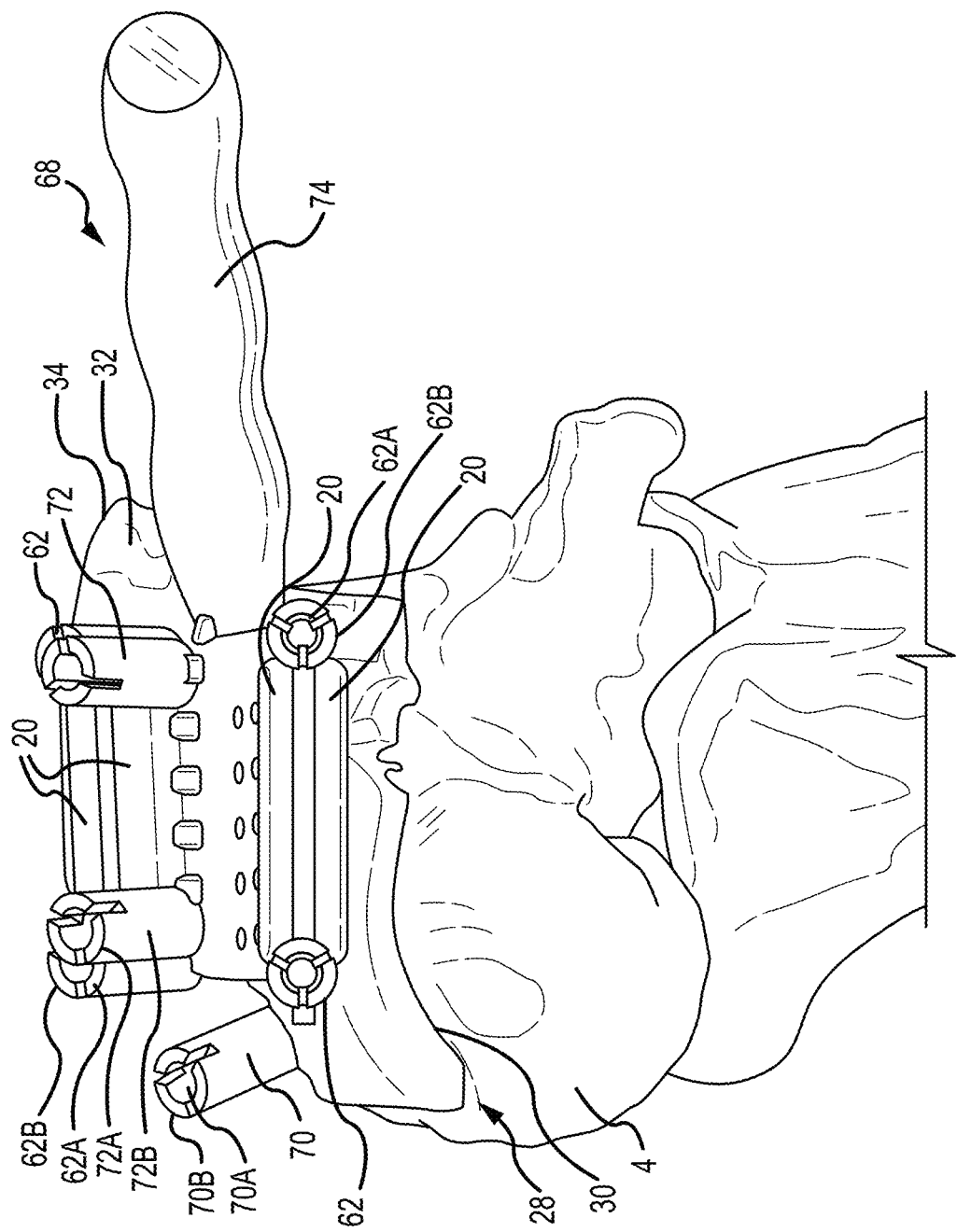
Figure 28:
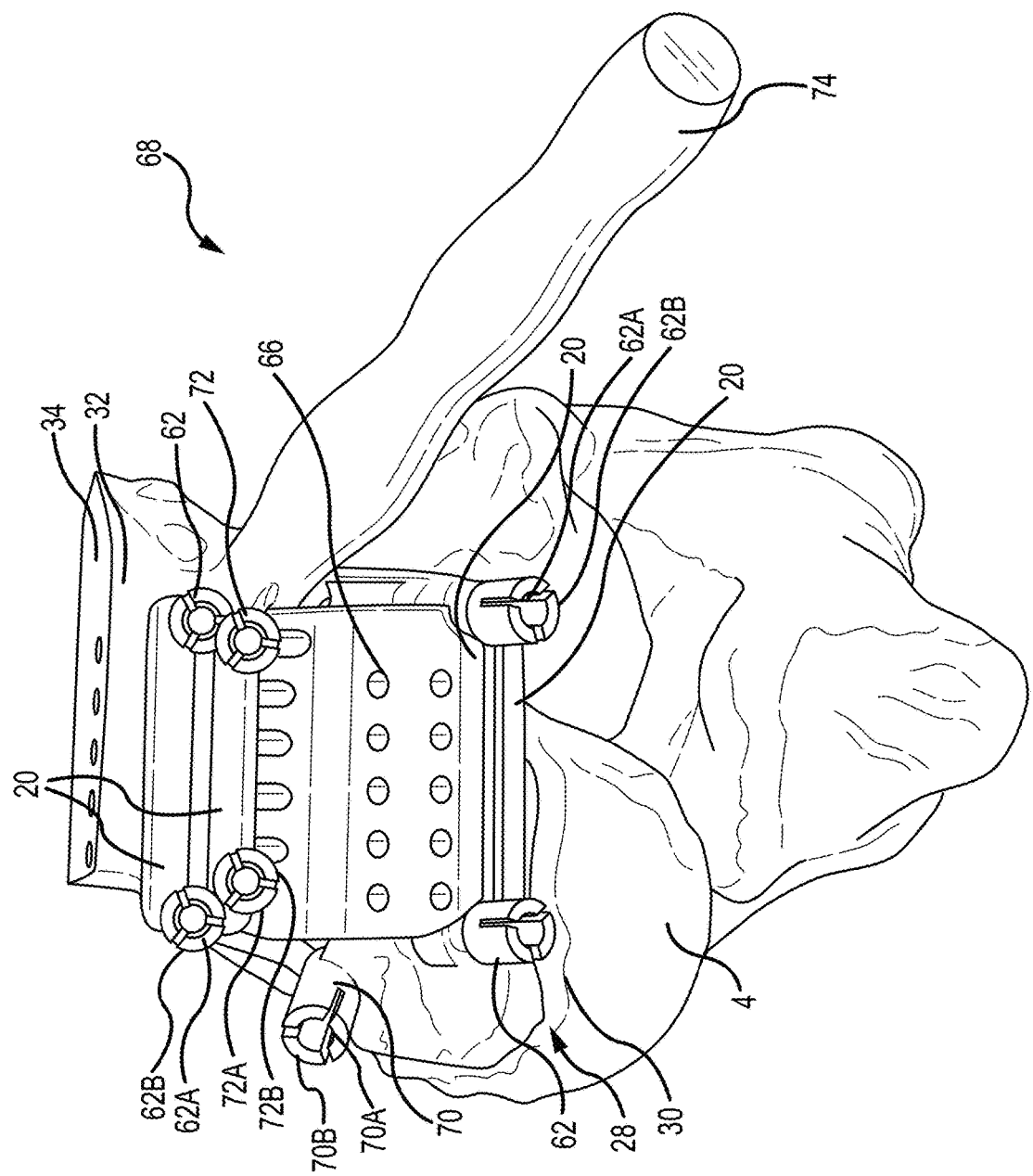
Figure 29:
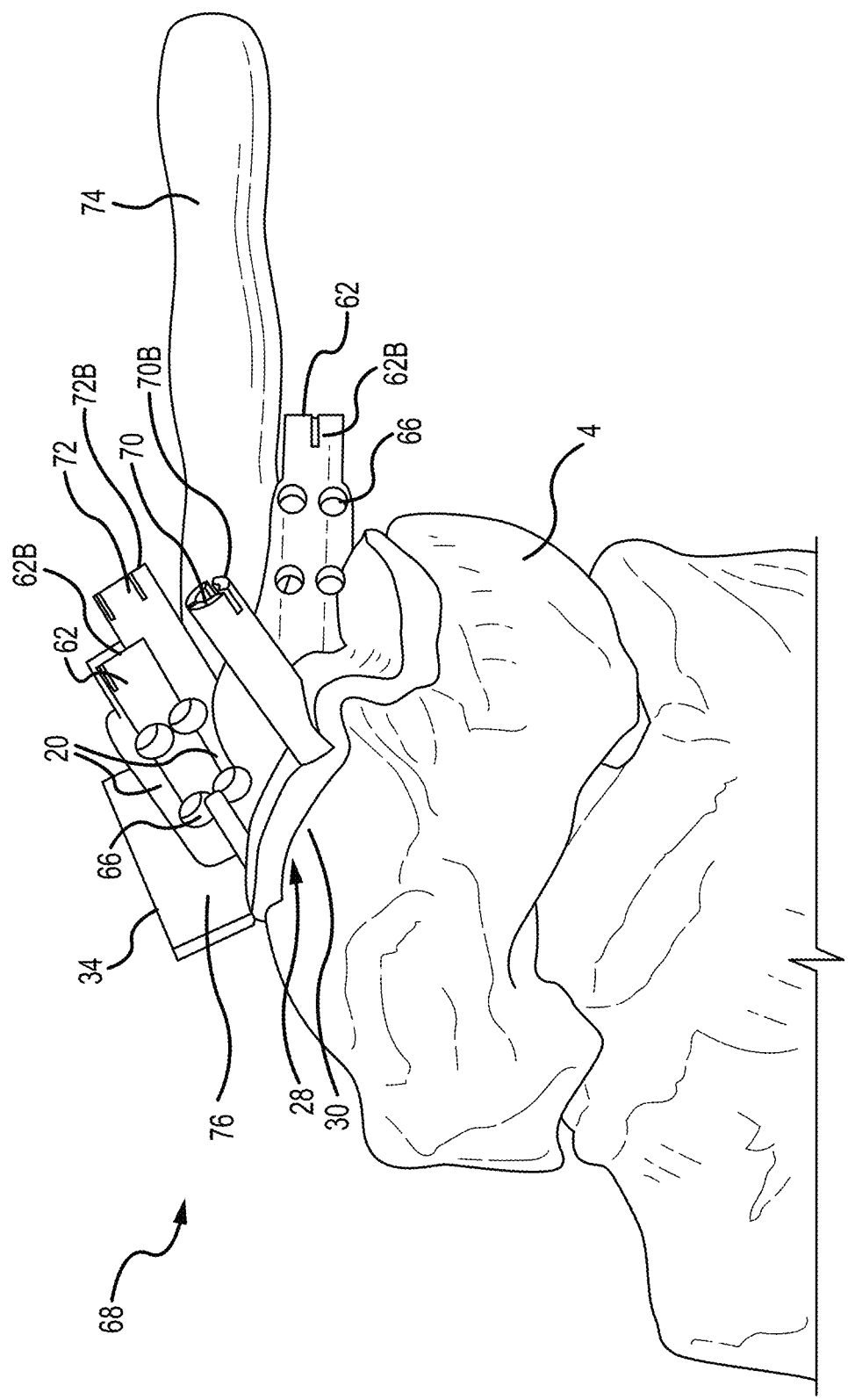
Figure 30:
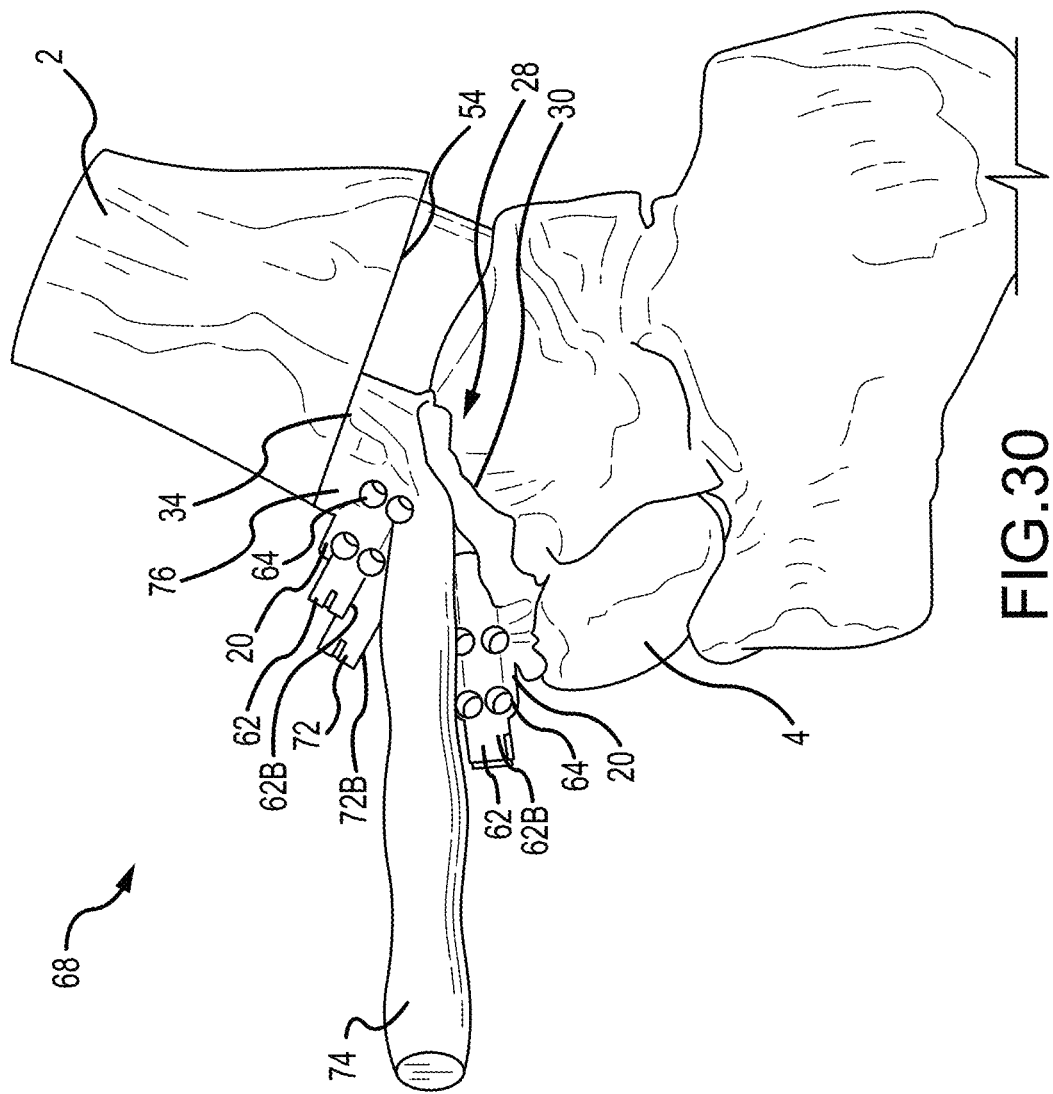
Figure 31:
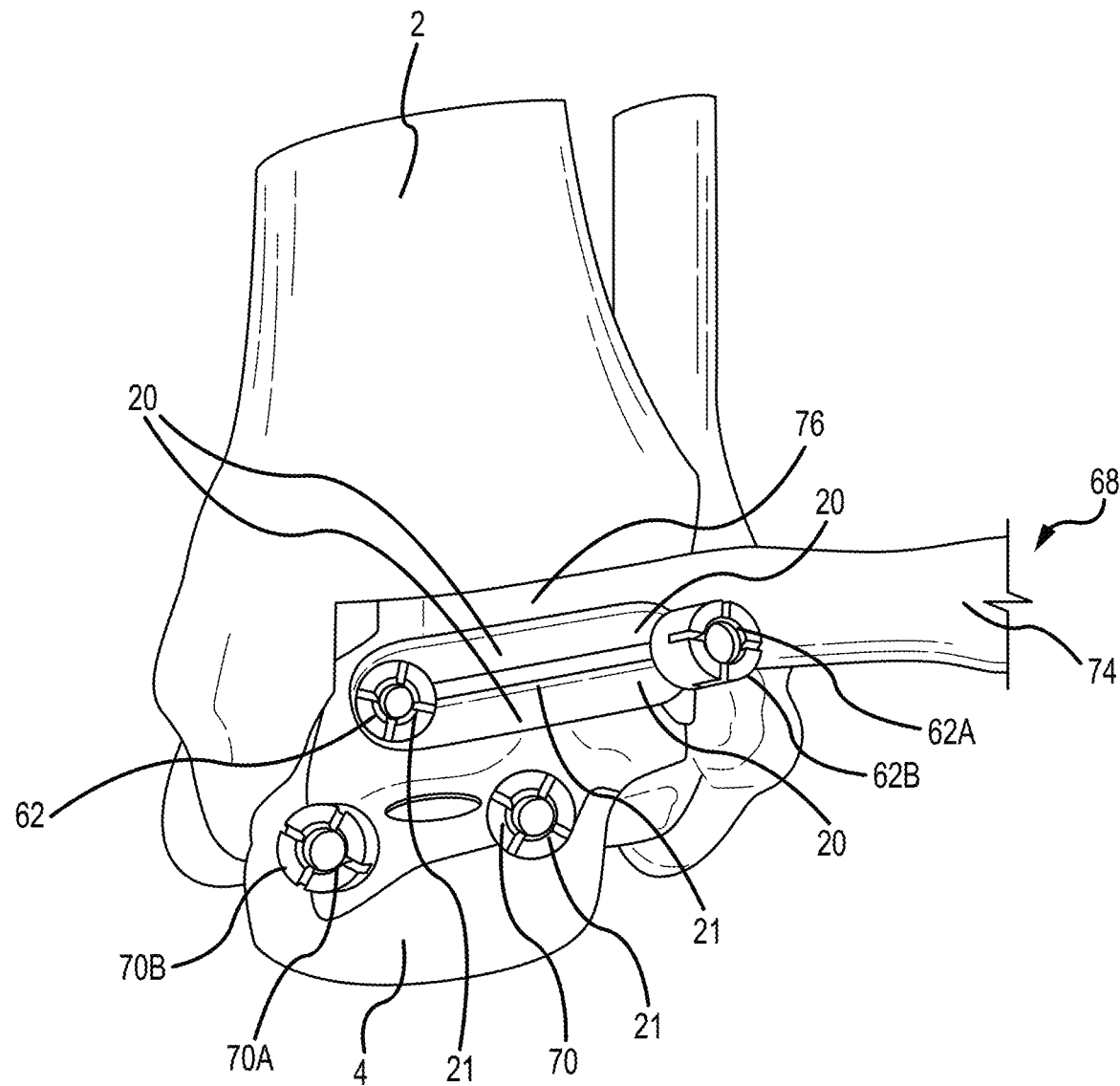
Figure 32:
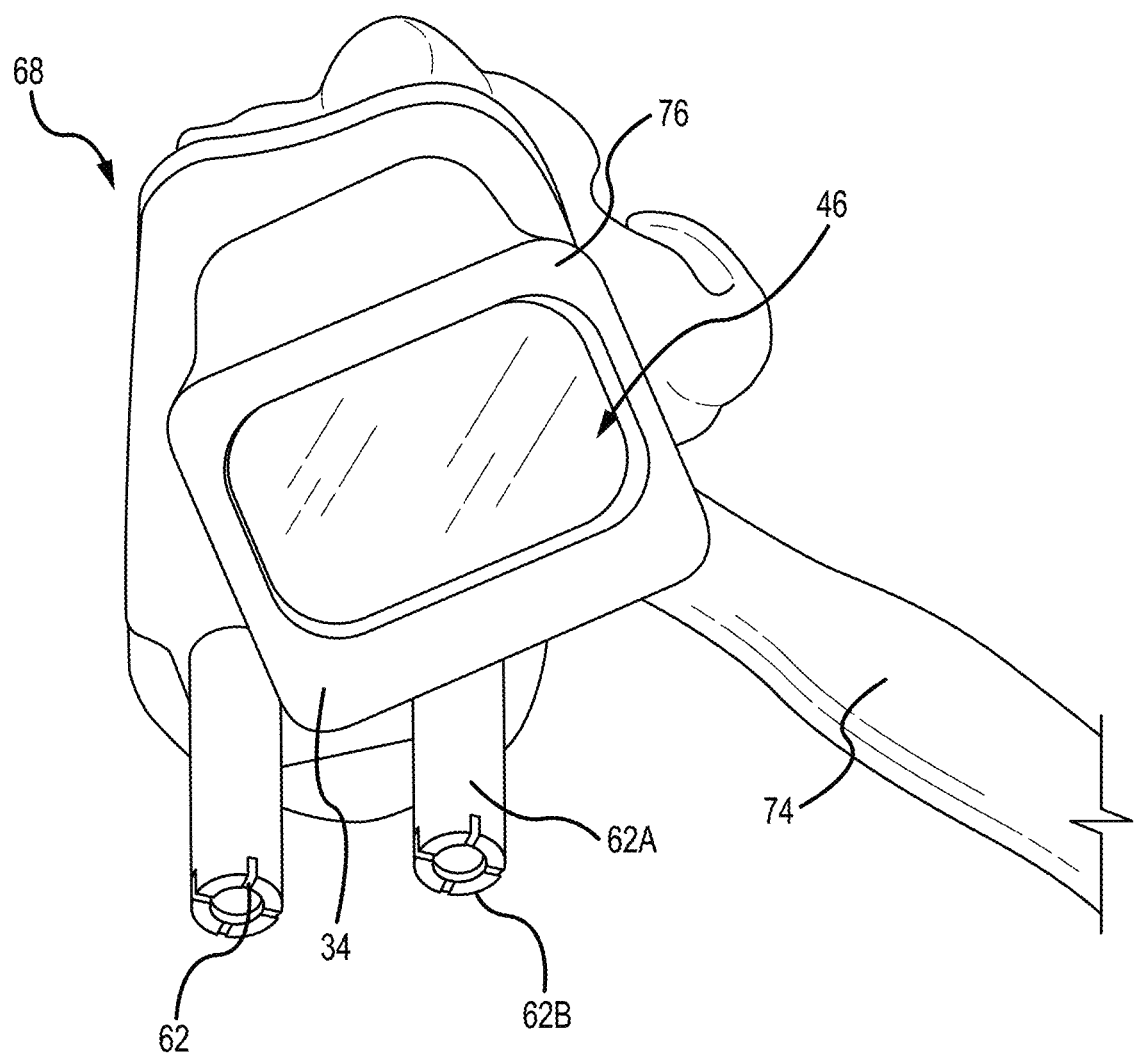
Figure 35:
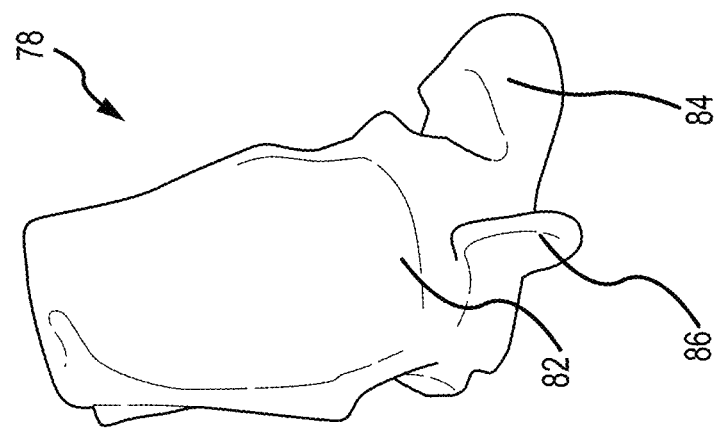
Figure 34:
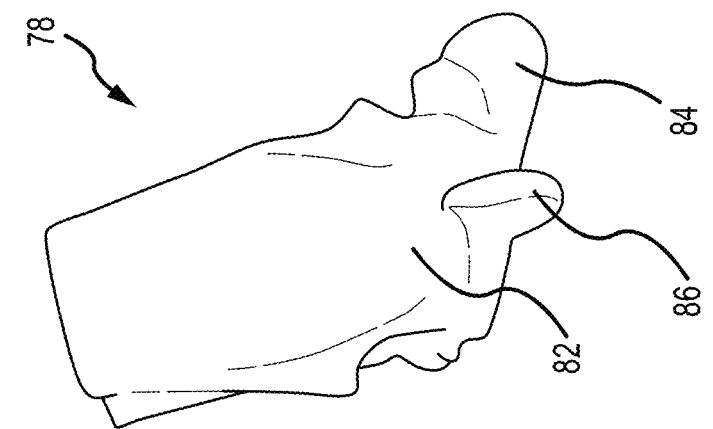
Figure 33:
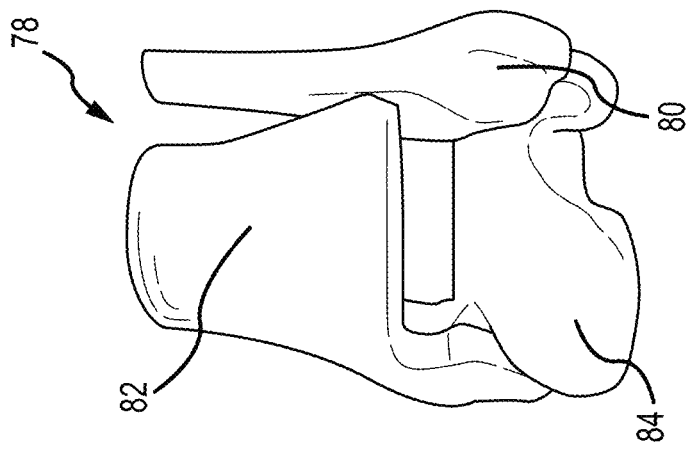

FIG. 1 depicts a lateral view of tibia and talus bones, with arrows indicating antero-posterior translation;

FIG. 2 depicts a top view of tibia and talus bones, with arrows indicating traverse rotation;

FIG. 3 depicts a medial oblique view of a tibial PSI, according to embodiments of the present disclosure;

FIG. 4 depicts a lateral oblique view of the tibial PSI of FIG. 3;

FIG. 5 depicts a lateral oblique view of a talar PSI, according to embodiments of the present disclosure;

FIG. 6 depicts a medial oblique view of the talar PSI of FIG. 5;

FIG. 7 depicts a first medial oblique view of a connection guide, according to embodiments of the present disclosure;

FIG. 8 depicts a second medial oblique view of the connection guide of FIG. 7;

FIG. 9 depicts a profile view of the tibial PSI of FIG. 3 attached to a tibia via pins, according to embodiments of the present disclosure;

FIG. 10 depicts a front view of the tibial PSI of FIG. 9 attached to the tibia via the pins, with distal connectors of the tibial PSI detached;

FIG. 11 depicts a profile view of the tibial PSI of FIG. 10 attached to the tibia via the pins, with a distal portion of the tibia resected;

FIG. 12 depicts a profile view of the talar PSI of FIG. 5 attached to a talus via pins, according to embodiments of the present disclosure;

FIG. 13 depicts a profile view of an antero-posterior adjustment of the talus, with the talar PSI of FIG. 12 connected to the talus;

FIG. 14 depicts a top view of a transversal rotation adjustment of the talus, with the talar PSI of FIG. 12 connected to the talus;

FIG. 15 depicts a profile view of a discrepancy between the planned talus and the intra-operative situation, with the talar PSI of FIG. 12 connected to the talus;

FIG. 16 depicts a top view of the discrepancy between the planned talus and the intra-operative situation, with the talar PSI of FIG. 12 connected to the talus;

FIG. 17 depicts a profile view of pins inserted through drilling apertures of the tibial PSI of FIG. 3 and the tibia, and pins inserted through drilling apertures of the talar PSI of FIG. 5 and the talus, according to embodiments of the present disclosure;

FIG. 18 depicts a front view of the pins inserted through the drilling apertures of the tibial PSI of FIG. 17 and the tibia, and the pins inserted through the drilling apertures of the talar PSI of FIG. 17 and the talus;

FIG. 19 depicts a profile view of the connection guide of FIG. 7 positioned on pins inserted through drilling apertures of the talar PSI of FIG. 5 and the talus, according to embodiments of the present disclosure;

FIG. 20 depicts a profile view of the connection guide of FIG. 19 positioned on pins inserted through the tibia, and on pins inserted through drilling apertures of the talar PSI of FIG. 19 and the talus;

FIG. 21 depicts a profile view of the pins inserted through the tibia and pins inserted through the talus after removal of PSI;

FIG. 22 depicts a front view of a tibial PSI positioned on a resected tibia, in accordance with embodiments of the present disclosure;

FIG. 23 depicts a first side view of the tibial PSI of FIG. 22 and the resected tibia;

FIG. 24 depicts a second side view of the tibial PSI of FIG. 22 and the resected tibia;

FIG. 25 depicts a front view of a tibial PSI positioned on a tibia, in accordance with embodiments of the present disclosure;

FIG. 26 depicts a perspective view of the tibial PSI of FIG. 25 positioned on the tibia;

FIG. 27 depicts a top view of a talar PSI with a handle positioned on a talus, in accordance with embodiments of the present disclosure;

FIG. 28 depicts a perspective view of the talar PSI of FIG. 27 positioned on the talus;

FIG. 29 depicts a first profile view of the talar PSI of FIG. 27 positioned on the talus;

FIG. 30 depicts a second profile view of the talar PSI of FIG. 27 positioned on the talus, and a resected tibia;

FIG. 31 depicts a perspective view of a talar PSI positioned on a talus, in accordance with embodiments of the present disclosure;

FIG. 32 depicts a top view of the talar PSI of FIG. 31 positioned on the talus;

FIG. 33 depicts a front view of a flexible bone model, in accordance with embodiments of the present disclosure;

FIG. 34 depicts a profile view of the flexible bone model of FIG. 33 at a first angle of flex; and FIG. 35 depicts the profile view of the flexible bone model of FIG. 34 at a second angle of flex.

DETAILED DESCRIPTION

Embodiments of the present disclosure include improved systems and methods for arthroplasty. In embodiments, the systems and method for arthroplasty include Patient Specific Instruments (PSI) which are mapped to a particular patient, such that observed abnormalities of the anatomy of the patient of the anatomy of the patient may be taken into consideration. In addition, the PSI of the present disclosure should allow for flexibility during arthroplasty, where additional or increased abnormalities in the anatomy of the patient are observed during the operation.

As described throughout the present disclosure, the various tibial PSI, talar PSI, and connection guides may be considered components of a PSI system. In addition, it is noted the connection guide may be considered a PSI, for purposes of the present disclosure. Further, it is noted the tibial PSI, the talar PSI, and/or the connection guide may be unique to a patient (or subset of patients) or alternatively may be a universal part of the PSI system usable with any other tibial PSI, talar PSI, and/or connection guide. Further, it is noted pins or connection rods as described throughout the disclosure may be unique to a patient or alternatively may be a universal part of the PSI system usable with any tibial PSI, talar PSI, and/or connection guide.

As described throughout the present disclosure, the PSI may include negative 3D structures of a patient's anatomy. For example, at least a portion of the tibial PSI and/or the talar PSI may be designed to conform and/or be modelled to a corresponding section of a tibia 2 and/or a talus 4, respectively. For example, the negative 3D structures may be reconstructed in three dimensions (3D) from slices of a computed (or computerized) tomography (CT) scan or from a magnetic resonance imaging (MM) scan, and the guides mirrors the shape of the 3D reconstruction. It is noted the MM scan may need to be of a certain accuracy (e.g., less than one millimeter (mm) cut). The components of the PSI system including, but not limited to, the tibial PSI, the talar PSI, and/or the connection guide may be fabricated via 3D printing, molding, casting, machining, or other additive manufacturing processes. For example, the PSI described throughout the present disclosure may be 3D printed in a thermoplastic (e.g., polyamide, nylon, or the like).

FIGS. 3 and 4 depict a tibial PSI 6, according to embodiments of the present disclosure. The tibial PSI 6 includes an upper portion 8 which is contoured to conform to the tibia 2. The upper portion 8 may include a tibial PSI interior surface 10 which is contoured to conform to a tibial contact surface 12 of the tibia 2. The mapping or contouring of the tibial PSI interior surface 10 to the tibial contact surface 12 of the tibia 2 may allow for the proper positioning and holding in place of the tibial PSI 6 proximate to or against the tibia 2. In addition, the mapping or contouring may indicate the tibial PSI 6 is mispositioned on the tibia 2 (e.g., by not fitting appropriately against or proximate to the tibia 2, or the like). The upper portion 8 may include a tibial PSI exterior surface 14 opposite the tibial PSI interior surface 10. For example, the tibial PSI exterior surface 14 may be similarly contoured to conform to the tibial contact surface 12 of the tibia 2. Alternatively, the tibial PSI exterior surface 14 may be differently contoured (or non-matching) to the tibial contact surface 12.

The tibial PSI 6 includes at least one proximal drilling aperture 16 and/or at least one distal drilling aperture 18. For example, the at least one proximal drilling aperture 16 and/or the at least one distal drilling aperture 18 may operate as a guide for a drilling device (e.g., a drill bit, or the like) to engage the tibia 2 at a particular location on a surface (e.g., the tibial contact surface 12, or another surface) and/or at a particular angle to the surface of the tibia 2. By way of another example, the at least one proximal drilling aperture 16 and/or the at least one distal drilling aperture 18 may receive and guide a pin (e.g., a proximal connecting pin) which is inserted into or passes through the tibia 2. In this regard, the at least one proximate drilling aperture 16 and/or the at least one distal drilling aperture 18 may ensure accurate and precise positioning of the pins within the tibia 2 during intra-operative procedures, in conformity with the locations as selected during virtual pre-operative planning (or pre-planning).

Where the tibial PSI 6 includes multiple proximal drilling apertures 16 and/or multiple distal drilling apertures 18, the multiple apertures 16, 18 may be respectively set at pre-defined angles relative to one another. For example, the multiple proximal drilling apertures 16 may be parallel or substantially parallel relative to one another, and/or the multiple distal drilling apertures 18 may be parallel or substantially parallel relative to one another (e.g., the pre-defined angle being zero or approximately zero). By way of another example, the multiple proximal drilling apertures 16 may be set at a non-zero angle relative to one another, and/or the multiple distal drilling apertures 18 may be set at a non-zero angle relative to one another.

It is noted the at least one proximal drilling aperture 16 and the at least one distal drilling aperture 18 may be set at a pre-defined angle relative to one another. For example, the at least one proximal drilling aperture 16 and the at least one distal drilling aperture 18 may be parallel or substantially parallel relative to one another (e.g., the pre-defined angle being zero or approximately zero). By way of another example, the at least one proximal drilling aperture 16 and the at least one distal drilling aperture 18 may be set at a non-zero angle relative to one another.

The at least one proximal drilling aperture 16 and/or the at least one distal drilling aperture 18 may be set within the tibial PSI exterior surface 14 of the upper portion 8. It is noted, however, the at least one proximal drilling aperture 16 and/or the at least one distal drilling aperture 18 may extend outward a select distance from the tibial PSI exterior surface 14 via a respective channel 16A, 18A passing through a respective protrusion or guide 16B, 18B. For example, the protrusion or guide 16B, 18B may provide additional assistance in directing the drilling device and/or a pin to be positioned at the correct angle at the location on the surface of the tibia 2, by providing a third dimension to direct (e.g., as opposed to an aperture 16, 18 providing only two dimensions to direct, or more specifically providing only location on the surface and not angle). Where the upper portion 8 includes the protrusion or guide 16B, 18B, the protrusion or guide 16B, 18B may be fabricated as a single component with or integrated into the upper portion 8. Alternatively, the protrusion or guide 16B, 18B may be separately fabricated and coupled to the tibial PSI exterior surface 14 of the upper portion 8.

The tibial PSI 6 includes at least one cutting guide 20. For example, the at least one cutting guide 20 may provide support for a cutting device (e.g., a saw, a blade, or the like) to engage the tibia 2 at a particular location on a surface (e.g., the tibial contact surface 12) and/or at a particular angle to the surface of the tibia 2. In this regard, the at least one cutting guide 20 may ensure accurate and precise positioning of the cutting device on the tibia 2 during intra-operative procedures, in conformity with the locations as selected during virtual pre-operative planning. In one non-limiting example, the cutting device may be usable to resect the tibia 2.

It is noted the at least one proximal drilling aperture 16, the at least one distal drilling aperture 18 (and/or the channels 16A, 18A within the protrusions or guides 16B, 18B), and/or the at least one cutting guide 20 may be lined with or otherwise include a protective guide 21. For example, the protective guide 21 may be fabricated from a metal or another material able to withstand forces applied by a drilling device or cutting device. In this regard, the tibial PSI 6 may not lose material if inadvertently cut, rubbed, or otherwise damaged by the drilling device or cutting device, thus reducing or preventing the possibility of contaminants inserted into the body of the patient during intra-operative procedures.

The tibial PSI 6 includes at least one additional contact 22. The at least one additional contact 22 may be coupled to the upper portion 8 via at least one connector 24. For example, the at least one connector 24 may couple the at least one additional contact 22 to the at least one cutting guide 20. It is noted the at least one additional contact 22 may operate as an additional cutting guide (e.g., where the cutting device is inserted between the at least one cutting guide 20 and the at least one additional contact 22).

In one non-limiting example embodiment, the tibial PSI 6 includes an upper portion 8 contoured to conform to the front face of the tibia 2. The upper portion 8 includes two proximal drilling apertures 16 with protrusions or guides 16B and channels 16A to guide pins through the tibia 2, two parallel distal drilling apertures 18 with protrusions or guides 18B and channels 18A to guide pins through the tibia 2, a cutting guide 20, and an additional contact 22 coupled to the upper portion 8 via two connectors 24. The additional contact 22 may increase stability of the tibial PSI 6 and provide a visual control for accurate and precise positioning of the tibial PSI 6, but is removable to allow for the resection of the tibia 2 during intra-operative procedures.

FIGS. 5 and 6 depict a talar PSI 26, according to embodiments of the present disclosure. The talar PSI 26 includes a talar PSI interior surface 28 which is contoured to conform to a talar contact surface 30 of the talus 4. The mapping or contouring of the talar PSI interior surface 28 to the talar contact surface 30 of the talus 4 may allow for the proper positioning and holding in place of the talar PSI 26 proximate to or against the talus 4. In addition, the mapping or contouring may indicate the talar PSI 26 is mispositioned on the talus 4 (e.g., by not fitting appropriately against or proximate to the talus 4, or the like). The talar PSI 26 includes a talar PSI exterior surface 32. For example, the talar PSI 26 exterior surface 32 may replicate a portion of the tibia 2 (e.g., a portion which was resected or otherwise removed from the tibia 2). Alternatively, the talar PSI exterior surface 32 may be differently contoured (or non-matching) to the portion of the tibia 2.

It is noted the talar PSI 26 may be a thickness extending above the talar contact surface 30. The talar PSI 26 may include a talar PSI gap surface 34 (or proximal surface 34) at a point a select distance above the talar contact surface 30. The talar PSI gap surface 34 may conform to a surface on the tibia 2. For example, the surface may be the cut surface following removal or resection of part of the tibia 2. It is noted the talar PSI interior surface 28 conforming to the talar contact surface 30 and the talar PSI gap surface 34 also conforming to the surface of the tibia 2 may require the thickness of the talar PSI 26 above the talar contact surface 30 to vary, as the gap between the tibia 2 and the talus 4 may similarly vary. In this regard, the talar PSI 26 may be inserted between and support the tibia 2 and/or the talus 4 during intra-operative procedures.

The talar PSI 26 includes at least one drilling aperture 36. For example, the at least one drilling aperture 36 may operate as a guide for a drilling device (e.g., a drill bit, or the like) to engage the talus 4 at a particular location on a surface (e.g., the talar contact surface 30, or another surface) and/or at a particular angle to the surface of the talus 4. By way of another example, the at least one drilling aperture 36 may receive and guide a pin (e.g., a connecting pin) which is inserted into or passes through the talus 4. In this regard, the at least one drilling aperture 36 may ensure accurate and precise positioning of the pins within the talus 4 during intra-operative procedures, in conformity with the locations as selected during virtual pre-operative planning. It is noted the drilling aperture 36 may be considered an alignment drilling aperture, for purposes of the present disclosure.

Where the talar PSI 26 includes multiple drilling apertures 36, the multiple drilling apertures 36 may be respectively set at pre-defined angles relative to one another. For example, the multiple drilling apertures 36 may be parallel or substantially parallel relative to one another (e.g., the pre-defined angle being zero or approximately zero). By way of another example, the multiple drilling apertures 36 may be set at a non-zero angle relative to one another.

The at least one drilling aperture 36 may be set within the talar PSI exterior surface 32. It is noted, however, the at least one drilling aperture 36 may extend outward a select distance from the talar PSI exterior surface 32 via a channel 36A passing through a protrusion or guide 36B. For example, the protrusion or guide 36B may provide additional assistance in directing the drilling device and/or a pin to be positioned at the correct angle at the location on the surface of the talus 4, by providing a third dimension to direct (e.g., as opposed to a drilling aperture 36 providing only two dimensions to direct, or more specifically providing only location on the surface and not angle). Where the talar PSI 26 includes the protrusion or guide 36B, the protrusion or guide 36B may be fabricated as a single component with or integrated into the talar PSI exterior surface 32. Alternatively, the protrusion or guide 36B may be separately fabricated and coupled to the talar PSI exterior surface 32.

It is noted the at least one drilling aperture 36 (and/or the channel 36A within the protrusions or guide 36B) may be lined with or otherwise include a metal or another material able to withstand forces applied by a drilling device. In this regard, the talar PSI 26 may not lose material if inadvertently cut, rubbed, or otherwise damaged by the drilling device, thus reducing or preventing the possibility of contaminants inserted into the body of the patient during intra-operative procedures.

In one non-limiting example embodiment, the talar PSI 26 includes surfaces 28, 32, and 34. The talar PSI interior surface 28 conforms to the talus 4 on the forefront half articular surface, plus the talar neck. The talar PSI gap surface 34 conforms to a planar surface on the distal tibia created via a cutting device (e.g., with the assistance of the tibial PSI 6). The talar PSI exterior surface 32 is modeled after the front face of the tibia 2 (e.g., the portion of the front face removed via resection) so that the talar PSI 26 may be accurately and precisely positioned relative to the tibia 2. The talar PSI exterior surface 32 also provides a visual control to assess the conformity of the intra-operative procedure, as compared to the virtual pre-operative planning.

FIGS. 7 and 8 depict a connection guide 38, according to embodiments of the present disclosure. The connection guide 38 includes a body 40. The body 40 includes a front surface 42 and a rear surface 44. For example, the body 40 may fabricated from solid material having a defined perimeter and set thickness. It is noted, however, at least a portion of the body 40 may be removed either during fabrication or after fabrication, and/or may not be fabricated at all. For example, the body 40 may include at least one defined cavity 46. The removed material may provide access to the underlying bone structure for access with a surgical tool (e.g., a reamer, a drill, a saw or blade, or the like). By way of another example, he removed material may provide the body 40 with a desired level of flexibility (e.g., by producing living hinges in portions of the body). By way of another example, the removal material may reduce the overall weight and/or cost of the connection guide 38 (and thus the PSI system, as a whole). It is noted the cavity 46 may allow for access to the tibia 2 and/or the talus 4 when the connection guide 38 is installed on the pins 50 (e.g., for visual confirmation of positioning of the PSI relative to the bones, to allow for access with a metallic reamer, of the like).

The connection guide 38 includes at least one guide aperture 48. For example, the at least one guide aperture 48 may receive pins which are inserted into or pass through the tibia 2 and/or the talus 4. By way of another example, the at least one guide aperture 48 may operate as a guide for a drilling device (e.g., a drill bit, or the like).

Where the connection guide 38 includes multiple guide apertures 48, the multiple guide apertures 48 may be respectively set at pre-defined angles relative to one another. For example, the multiple guide apertures 48 may be parallel or substantially parallel relative to one another (e.g., the pre-defined angle being zero or approximately zero). By way of another example, the multiple guide apertures 48 may be set at a non-zero angle relative to one another.

The at least one guide aperture 48 may be set within the front surface 42 and/or the rear surface 44. It is noted, however, the at least one guide aperture 48 may extend outward a select distance from the front surface 42 via a channel 44A passing through a protrusion or guide 44B. For example, the protrusion or guide 44B may provide additional assistance in aligning the connection guide 38 with the pins installed in or passing through the tibia 2 and/or the talus 4, by providing a third dimension to direct (e.g., as opposed to a guide aperture 48 providing only two dimensions to direct, or more specifically providing only location on the surface and not angle). Where the connection guide 38 includes the protrusion or guide 44B, the protrusion or guide 44B may be fabricated as a single component with or integrated into the front surface 42. Alternatively, the protrusion or guide 44B may be separately fabricated and coupled to the front surface 42.

It is noted the at least one guide aperture 48 (and/or the channel 44A within the protrusions or guide 44B) may be lined with or otherwise include a metal or another material able to withstand forces applied by a drilling device. In this regard, the connection guide 38 may not lose material if inadvertently cut, rubbed, or otherwise damaged by the drilling device, thus reducing or preventing the possibility of contaminants inserted into the body of the patient during intra-operative procedures.

It is noted the positioning of the at least one guide aperture 48 may be pre-defined to align with the at least one proximal drilling aperture 16 and/or the at least one distal drilling aperture 18 of the tibial PSI 6, and/or the at least one drilling aperture 36 of the talar PSI 26. In this regard, the at least one guide aperture 48 may ensure accurate and precise positioning of the connection guide 38 on the pins within the tibia 2 and/or the talus 4 during intra-operative procedures. The connection guide 38 may provide a solution to couple the tibial PSI 6 and the talar PSI 26 together, acting as a securing device and preventing the movement of one PSI relative to another. Similarly, the connection guide 38 may provide a solution to prevent the movement of the tibia 2 and the talus 4 relative to one another, when pins are installed within them, while also ensuring the correct positioning of the tibia 2 and talus 4 via the guidance provided by the installed pins.

In embodiments where the tibial PSI 6 includes the protrusions or guides 16B, 18B and/or the talar PSI 26 includes the protrusions or guides 36B, the rear surface 44 may include at least one recess dimensioned to at least partially receive the protrusions or guides 16B, 18B, 36B. In this regard, the connection guide 38 may at least partially couple directly to the tibial PSI 6 and/or talar PSI 26, provide an increased level of security in addition to indirectly being coupled together via the pins passing through the at least one guide aperture 48, while also allowing for a more compact package when installed. It is noted, however, the rear surface 44 may be planar or substantially planar, such that the protrusions or guides 16B, 18B, 36B rest against the rear surface 44 when the connection guide 38 is installed on pins in front of the tibial PSI 6 and/or talar PSI 26.

In one non-limiting example embodiment, the connection guide 38 is designed with four parallel (or substantially parallel) and perpendicular (or substantially perpendicular) guide apertures 48. Two upper guide apertures 48 are aligned with two pins positioned within the tibia 2 by the tibial PSI 6. Two lower guide apertures 48 are aligned with two pins positioned within the talus 4 by the talar PSI 26.

FIGS. 9-21 generally depict a method or procedure of using the PSI described throughout the present disclosure. It is noted the method or procedure generally illustrated in FIGS. 9-21 utilizes the PSI system including the tibial PSI 6, the talar PSI 26, and the connection guide 38 as described in one or more embodiments throughout the present disclosure, and includes one or more of the following steps. It is noted any components of any system-level or apparatus-level embodiment of the present disclosure may be configured to perform or be used for one or more of the following steps or embodiments, and vice versa.

In one embodiment of the present disclosure, the method may include, but is not limited to, commencing an operation with the tibia 2 and aligning the talus 4 under the tibia 2. The method may include procedures to attach the tibial PSI 6 to the tibia 2, the talar PSI 26 to the talus 4, installing the connection guide 38, installing pins or rods within the tibia 2 and/or the talus 4 via the tibial PSI 6 and/or the talar PSI 26 respectively, and/or removing one or more components of the PSI system from installed pins or rods.

FIGS. 9-11 depicts a procedure of attaching the tibial PSI 6 to the tibia 2 via at least one distal pin 50, according to embodiments of the present disclosure. Although not depicted in FIGS. 9-11, the procedure contemplates the tibial PSI 6 is already provided or installed on the tibia 2 in an accurate and precise location due to the various conforming contact surfaces of the tibia 2 and the tibial PSI 6 as described throughout the disclosure.

In FIG. 9, at least one distal pin 50 is installed via the at least one distal drilling aperture 18 of the tibial PSI 6 to couple the tibial PSI 6 to the tibia 2. The tibia 2 is drilled via the at least one distal drilling aperture 18. The at least one distal pin 50 is installed in the tibia 2 (e.g., via threading, pressure, friction, an applied force, or the like) through the upper portion 8. It is noted the tibial PSI exterior surface 14 may provide visual control to align the tibial PSI 6 with the tibia 2 when drilling for the at least one distal pin 50.

In FIG. 10, the at least one additional contact 22 is removed from the upper portion 8 of the tibial PSI 6. The at least one connector 24 may be cut or otherwise broken, so that the at least one additional contact 22 is detached from the upper portion 8. As the at least one distal pin 50 was installed through the upper portion 8, the upper portion 8 remains in place after the at least one additional contact 22 is removed.

In FIG. 11, a bone cutting takes place to remove a thin layer of tibia 2, allowing for a wider view of the talar articular surface. The cutting guide 20 provides a guide for a cutting device to make the bone cutting. For example, a bottom surface 52 of the cutting guide 20 and a resected surface 54 of the tibia 2 may be planar or substantially planar, as the bottom surface 52 of the cutting guide 20 formed the guide for the cut making the resected surface 54 of the tibia 2.

FIGS. 12-16 depicts a procedure of attaching the talar PSI 26 to the talus 4 via at least one alignment pin 50, according to embodiments of the present disclosure. Although not depicted in FIGS. 12-16, the procedure contemplates the talar PSI 26 is already provided or installed on the talus 4 in an accurate and precise location due to the various conforming contact surfaces of the talus 4 and the talar PSI 26 as described throughout the disclosure.

In FIG. 12, at least one alignment pin 50 is installed via the at least one drilling aperture 36 of the talar PSI 26 to couple the talar PSI 26 to the talus 4. The talus 4 is drilled via the at least one drilling aperture 36. The at least one alignment pin 50 is installed in the talus 4 (e.g., via threading, pressure, friction, an applied force, or the like). It is noted the talar PSI exterior surface 32 may provide visual control to align the talar PSI 26 with the talus 4 when drilling for the at least one alignment pin 50. It is noted the tibial PSI 6 may be removed from the tibia 2 by sliding along the at least one distal pin 50 in the tibia 2 either prior to or after the alignment and coupling of the talar PSI 26 to the talus 4.

In FIGS. 13 and 14, the talus 4 and the talar PSI 26 are adjusted with the at least one alignment pin 50 inserted in the talus 4 in such a way that the proximal planar face or talar PSI gap surface 34 contacts the resected surface 54 of the tibia 2. For example, as depicted in FIG. 13, the talus 4 and the talar PSI 26 may be adjusted through antero-posterior translation. By way of another example, as depicted in FIG. 14, the talus 4 and the talar PSI 26 may be adjusted through transversal rotation. Alternatively or in addition, the talus 4 and the talar PSI 26 may be adjusted in such a way that the talar PSI exterior surface 32 designed to mimic the resected portion of the tibia 2 is aligned with the tibia 2. Further, a planar surface replicating a front face of the tibia 2 on the talus 4 may be aligned on the anterior cortex of the tibia 2. It is noted the alignment of the talus 4 and the talar PSI 26 is designed to replicate the virtual positioning of the tibia 2 and talus 4 during the virtual pre-operative planning stage of the operation (e.g., via software). In addition, it is noted the adjustment of the talus 4 and the talar PSI 26 may be completed with the at least one distal pin 50 inserted in the tibia 2, or with the at least one distal pin 50 removed from the tibia 2.

FIGS. 15 and 16 depict an example where the alignment is not consistent with the virtual positioning set during the virtual pre-operative planning stage of the operation. In FIGS. 15 and 16, the tibia 2 is misaligned in the posterior direction relative to the talus 4 and the talar PSI 26. The talus 4 and the talar PSI 26 may be adjusted in the posterior direction relative to the tibia 2. In this regard, the PSI system allows for a freedom of movement with respect to antero-posterior translation and/or transversal rotation of the talus 4 and the talar PSI 26 relative to the tibia 2. It is noted FIG. 16 may include pins 50 which are not correctly aligned with the at least one drilling hole 36, illustrating the interference that would occur if the pins 50 were inserted into the at least one drilling hole 36 with the talar PSI 26 oriented as depicted.

FIGS. 17 and 18 depicts a process of re-attaching the tibial PSI 6 to the tibia 2 via at least one pin 50, according to embodiments of the present disclosure. If the alignment is consistent with the virtual positioning set during the virtual pre-operative planning stage, the tibial PSI 6 is slid onto the at least one distal pin 50 set within the tibia 2 and re-coupled to the tibia 2. For example, the bottom surface 52 of the cutting guide 20, the resected surface 54 of the tibia 2, and the talar PSI gap surface 34 of the talar PSI 26 may all be in contact. The tibia 2 is drilled with at least one proximal drilling aperture 16. It is noted the tibial PSI exterior surface 14 may provide visual control to align the tibial PSI 6 with the tibia 2 when sliding the tibial PSI 6 onto the at least one distal pin 50 and drilling for the at least one proximal pin 50 of the tibia 2.

FIGS. 19 and 20 depicts a process of attaching the connection guide 38 and the talar PSI 26 to the talus 4 via the pins 50, according to embodiments of the present disclosure. Although not depicted in FIGS. 19 and 20, the procedure contemplates the tibial PSI 6 is removed prior to the attaching of the connection guide 38.

In FIG. 19, the connection guide 38 is slid onto the at least one alignment pin 50 installed in the talus 4. The at least one alignment pin 50 inserted in the talus 4 is passed through at least one guide aperture 48 of the connection guide 38.

In FIG. 20, at least one proximal pin 50 is installed in the tibia 2 (e.g., via threading, pressure, friction, an applied force, or the like). The at least one proximal pin 50 is installed via the at least one proximal drilling aperture 16 of the tibial PSI 6 to further couple the tibial PSI 6 to the tibia 2. The at least one proximal pin 50, previously drilled for when the tibial PSI 6 was coupled to the tibia 2 via the at least one distal pin 50, are inserted into the tibia 2 by being passed through at least a second guide aperture 48 of the connection guide 38. It is contemplated, however, the at least one proximal pin 50 may be inserted into the tibia 2 prior to the removal of the tibial PSI 6 and the installation of the connection guide 38.

FIG. 21 depicts the pins 50 inserted through the tibia 2 and pins 50 inserted through the talus 4 after removal of the tibial PSI 6, the talar PSI 26, and the connection guide 38, according to embodiments of the present disclosure. The connection guide 38 and the talar PSI 26 are removed from the tibia 2 and the talus 4 after the insertion of the at least one proximal pin 50 in the tibia 2. Following the removal of the components of the PSI system, the pins 50 are left inserted in the tibia 2 and the talus 4 for supporting metallic guides used in further procedures in the operation.

As illustrated in FIGS. 9-21, the pins 50 may include one or multiple diameters. For example, the pins 50 may include a first section with a first diameter, and a second section with a second diameter. For instance, the first section may be greater in diameter than the second section. It is contemplated that the greater diameter section may be formed with the lesser diameter section, or may alternatively be a separate component (e.g., a collar or lock) which has a different diameter from the pin 50 and is couplable (e.g., slidable, clippable, or the like) to the pin 50.

It is noted any methods or procedures described throughout the disclosure may include more or fewer operations or embodiments than those described. In addition, it is noted the operations or embodiments of any methods or procedures may be performed at any time (e.g., sequentially, concurrently, or simultaneously). Further, it is noted the operations or embodiments of any methods or procedures may be performed in any order, including in an order as presented in the disclosure and/or an order other than that presented in the disclosure.

For example, in another embodiment of the present disclosure, the method may include, but is not limited to, commencing an operation with the tibia 2 and aligning the talus 4 under the tibia 2. The method may include procedures to attach the talar PSI 26 to the talus 4, attach the tibial PSI 6 to the tibia 2, installing the connection guide 38, installing pins or rods within the tibia 2 and/or the talus 4 via the tibial PSI 6 and/or the talar PSI 26 respectively, and/or removing one or more components of the PSI system from installed pins or rods. In this example method, the talus 4 is first modified using the talar PSI 26, and the tibia 2 is moved into place relative to the talus 4 using the tibial PSI 6.

At least one distal pin 50 is drilled through the most distal apertures of the talar PSI 26 to couple it to the talus 4. For example, two pins may be drilled. Connections are cut on the talar PSI 26 using known cutting devices and techniques to separate at least one additional contact from a main portion of the talar PSI 26. A bone cutting takes place to remove a thin layer of talus 4, creating a resected surface and allowing for a wider view of the tibial articular surface of the tibia 2.

The tibial PSI 6 is then positioned onto the tibia 2 in an accurate and precise position. At least one alignment pin is drilled through the drilling apertures. For example, two pins may be drilled. The talar PSI 26 is removed from the talus 4 by sliding it along its pins 50. The tibia 2 and the tibial PSI 6 is moved in such a way that a planar face of the tibial PSI 6 contacts the resected surface of the talus 4. In addition, the planar surface replicating a front face of the talus 4 is aligned on the anterior cortex of the tibia 2. It is noted the alignment of the tibia 2 and the tibial PSI 6 is designed to replicate the virtual positioning of the tibia 2 and talus 4 during the virtual pre-operative planning stage of the operation (e.g., via software).

If the alignment of the tibia 2 and the tibial PSI 6 is not consistent with the virtual positioning set during the virtual pre-operative planning stage of the operation, the tibia 2 and the tibial PSI 6 is adjusted through antero-posterior translation and/or transversal rotation relative to the talus 4. In this regard, the PSI system allows for a freedom of movement with respect to antero-posterior translation and/or transversal rotation of the tibia 2 and the tibial PSI 6 relative to the talus 4.

If the alignment is consistent with the virtual positioning set during the virtual pre-operative planning stage, the talar PSI 26 is slid onto the at least one distal pin 50 set within the talus 4 and re-coupled to the talus 4. The talus 4 is drilled with at least one proximal drilling aperture 16. It is noted one or more surfaces of the talar PSI 26 may provide visual control to align the talar PSI 26 with the talus 4 when sliding the talar PSI 26 onto the at least one distal pin 50 and drilling for the at least one proximal pin 50 of the talus 4.

A connection guide 38 is then slid onto the at least one alignment pin 50 installed in the tibia 2. The at least one pin 50 inserted in the tibia 2 is passed through at least one guide aperture 48 of the connection guide 38.

At least one proximal pin 50 is installed via at least one proximal aperture of the talar PSI 26 to further couple the talar PSI 26 to the talus 4. For example, two proximal pins 50 may be installed. The at least one proximal pin 50, previously drilled for when the talar PSI 26 was coupled to the talus 4 via the at least one distal pin 50, are inserted into the talus 4 by being passed through at least a second guide aperture 48 of the connection guide 38. It is contemplated, however, the at least one proximal pin 50 may be inserted into the talus 4 prior to the removal of the talar PSI 26 and the installation of the connection guide 38.

The connection guide 38 and the tibial PSI 6 are removed from the tibia 2 and the talus 4 after the insertion of the at least one proximal pin 50 in the talus 4. Following the removal of the components of the PSI system, the pins 50 are left inserted in the tibia 2 and the talus 4 for supporting metallic guides used in further procedures in the operation.

In general, the tibial PSI and the talar PSI as described throughout the present disclosure may be usable in a method for ankle arthroplasty including one or more of the following embodiments.

In embodiments, during pre-operative planning, relative positions of a tibia and a talus may be evaluated. A patient-specific instrument (PSI) system may be provided including a tibial PSI designed based on the tibia and a talar PSI designed based on the talus during the pre-operative planning.

In embodiments, during the pre-operative planning, the tibial PSI may be designed from a scan of the tibia and the talar PSI may be designed from a scan of the talus. A flexible bone model may be designed from the scan of the tibia and the scan of the talus. The flexible bone model includes a select range of articulation. The flexible bone model is operable to receive the tibial PSI and the talar PSI. The flexible bone model is operable to test the tibial PSI relative to the tibia and the talar PSI relative to the talus during simulated repositioning.

In embodiments, during an intra-operative procedure, the position of the tibia and talus may be compared, wherein the comparing is based on the relative positions of the tibia and the talus evaluated during the pre-operative planning and on observed positions of the tibia and the talus during the intra-operative procedure. The tibial PSI may be installed on the tibia and the talar PSI may be installed on the talus. At least one of the tibia via the tibial PSI or the talus via the talar PSI may be adjusted. The tibial PSI and the talar PSI may be removed.

In embodiments, during the intra-operative procedure, pins may be installed in the tibia via the tibial PSI and the talus via the talar PSI. At least some of the pins may be used with a connection guide to align the tibia and the talus.

FIGS. 22-26 depict a tibial PSI 56 positioned on a resected tibia 2, in accordance with embodiments of the present disclosure. Unless otherwise noted, the tibial PSI 56 has features that are the same as, or similar to, other embodiments of tibial PSI described throughout the present disclosure and operates in the same or similar manner. In this regard, embodiments directed to tibial PSI 6 should be interpreted as being applicable to the tibial PSI 56, and vice versa, unless otherwise noted. It is noted FIGS. 22-24 depict a first embodiment of the tibial PSI 56, while FIGS. 25 and 26 depict a second embodiment of the tibial PSI 56.

The tibial PSI 56 includes at least one viewing aperture or window 58. The at least one viewing aperture or window 58 may be utilized to ensure correct contact is being made by the tibial PSI 56 interior surface 10 and the tibial contact surface 12. The at least one viewing aperture or window 58 may be designed to accommodate abnormalities on the tibial contact surface 12 (e.g., where it would be more effective to surround the abnormalities with an opening as opposed to mapping or contouring to it with the tibial PSI interior surface 10). The at least one viewing aperture or window 58 may allow for reduced weight and material used during fabrication, allowing for reduced cost. The at least one viewing aperture or window 58 may provide access to the underlying bone structure for access with a surgical tool (e.g., a reamer, a drill, a saw or blade, or the like).

The tibial PSI 56 includes multiple cutting guides 20 (e.g., as opposed to a single cutting guide 20 as illustrated with the tibial PSI 6). In this regard, the tibial PSI 56 includes increased stability for the guiding of a cutting device. As the cutting guide 20 is within the upper portion 8 of the tibial PSI 56, however, the tibia 2 may need to be further cut or otherwise scored to resect as necessary for the operation. For example, the tibial PSI 56 may include a second set of cutting guides 20 which may at least partially intersect with a cut made by a cutting device via the first set of cutting guides 20. By way of another example, the tibial PSI 56 may include at least one stamping aperture 60 which may at least partially intersect with a cut made by a cutting device via the cutting guide 20. For example, the tibial PSI 56 may include three stamping apertures 60. By way of another example, the tibial PSI 56 may include four stamping apertures 60, where a fourth does not interfere or collide with the talus 4. In general, the tibial PSI 56 may include any number of stamping apertures that do not collide with the talus 4.

As the cutting guides 20 are within the upper portion 8, such that the distal end of the tibia 2 is cut a select distance up from the articular surface instead of being trimmed proximate to the talus 4, the tibial PSI 56 may include at least one protection aperture 62 surrounding or flanking the cutting guides 20. For example, pins inserted in the protection apertures 62 may protect the medial malleolus of the tibia 2 and/or the fibula.

Where the tibial PSI 56 includes multiple stamping apertures 60 and/or multiple protection apertures 62, the multiple apertures 60, 62 may be respectively set at pre-defined angles relative to one another. For example, the multiple stamping apertures 60 may be parallel or substantially parallel relative to one another, and/or the multiple protection apertures 62 may be parallel or substantially parallel relative to one another (e.g., the pre-defined angle being zero or approximately zero). By way of another example, the multiple stamping apertures 60 may be set at a non-zero angle relative to one another, and/or the multiple protection apertures 62 may be set at a non-zero angle relative to one another.

It is noted the at least one stamping aperture 60 and the at least one protection aperture 62 may be set at a pre-defined angle relative to one another. For example, the at least one stamping aperture 60 and the at least one protection aperture 62 may be parallel or substantially parallel relative to one another (e.g., the pre-defined angle being zero or approximately zero). By way of another example, the at least one stamping aperture 60 and the at least one protection aperture 62 may be set at a non-zero angle relative to one another.

The at least one stamping aperture 60 and/or the at least one protection aperture 62 may be set within the tibial PSI exterior surface 14 of the upper portion 8. It is noted, however, the at least one stamping aperture 60 and/or the at least one protection aperture 62 may extend outward a select distance from the tibial PSI exterior surface 14 via a respective channel 60A, 62A passing through a respective protrusion or guide 60B, 62B. For example, the protrusion or guide 60B, 62B may provide additional assistance in directing the drilling device and/or a pin to be positioned at the correct angle at the location on the surface of the tibia 2, by providing a third dimension to direct (e.g., as opposed to an aperture 60, 62 providing only two dimensions to direct, or more specifically providing only location on the surface and not angle). Where the upper portion 8 includes the protrusion or guide 60B, 62B, the protrusion or guide 60B, 62B may be fabricated as a single component with or integrated into the upper portion 8. Alternatively, the protrusion or guide 60B, 62B may be separately fabricated and coupled to the tibial PSI exterior surface 14 of the upper portion 8.

It is noted the at least one stamping aperture 60, the at least one protection aperture 62 (and/or the channels 60A, 62A within the protrusions or guides 60B, 62B), and/or the at least one cutting guide 20 may be lined with or otherwise include a protective guide 21, as described throughout the present disclosure. The tibial PSI 56 may include at least one guide aperture 64 for inserting the protective guide 21. It is noted, however, the tibial PSI 56 may be fabricated to allow for the insertion of the protective guide 21 via the tibial PSI interior surface 10 and/or the tibial PSI exterior surface 14.

Where the protective guide 21 is inserted in the tibial PSI 56 (and/or during fabrication of the tibial PSI 56 in general), residual fabrication or manufacturing material powder and/or cleaning powder may need to be removed from the tibial PSI 56. The tibial PSI 56 may include at least one cleaning aperture 66 for removing the residual fabricating material powder and/or cleaning powder (e.g., during a manufacturing process). It is noted a guide aperture 64 and a cleaning aperture 66 may be the same aperture utilized for different functions at different stages of the fabrication and use cycle for the tibial PSI 56.

FIG. 27-32 depict a talar PSI 68 with a handle positioned on a talus 4, in accordance with embodiments of the present disclosure. Unless otherwise noted, the talar PSI 68 has features that are the same as, or similar to, other embodiments of tibial PSI described throughout the present disclosure and operates in the same or similar manner. In this regard, embodiments directed to talar PSI 26 should be interpreted as being applicable to the talar PSI 68, and vice versa, unless otherwise noted. It is noted FIGS. 27-30 depict a first embodiment of the talar PSI 68, while FIGS. 31 and 32 depict a second embodiment of the talar PSI 68.

The talar PSI 68 includes at least one fixation aperture 70. For example, the at least one fixation aperture 70 may be utilized to receive a pin and hold the talar PSI 68 against the or proximate to the talus 4. It is noted the pin through the fixation aperture 70 may be removed when the talar PSI 68 is removed from the talus 4. The talar PSI 68 includes at least one tool guide aperture 72. For example, the at least one tool guide aperture 72 may be utilized to receive a pin and guide an anterior reaming metallic guide. For instance, the pin positioned by the at least one tool guide aperture 72 may be left in the talus 4 after removal of the talar PSI 68 for use when guiding the anterior reaming metallic guide. It is noted the at least one fixation aperture 70 and/or the at least one tool guide aperture 72 may perform a same or similar function as the at least one drilling aperture 36 as described with respect to the talar PSI 26.

Where the talar PSI 68 includes multiple fixation apertures 70 and/or multiple guide apertures 72, the multiple apertures 70, 72 may be respectively set at pre-defined angles relative to one another. For example, the multiple fixation apertures 70 may be parallel or substantially parallel relative to one another, and/or the multiple guide apertures 72 may be parallel or substantially parallel relative to one another (e.g., the pre-defined angle being zero or approximately zero). By way of another example, the multiple fixation apertures 70 may be set at a non-zero angle relative to one another, and/or the multiple guide apertures 72 may be set at a non-zero angle relative to one another.

It is noted the at least one fixation aperture 70 and the at least one tool guide aperture 72 may be set at a pre-defined angle relative to one another. For example, the at least one fixation aperture 70 and the at least one tool guide aperture 72 may be parallel or substantially parallel relative to one another (e.g., the pre-defined angle being zero or approximately zero). By way of another example, the at least one fixation aperture 70 and the at least one tool guide aperture 72 may be set at a non-zero angle relative to one another.

The at least one fixation aperture 70 and/or the at least one tool guide aperture 72 may be set within a surface of the talar PSI 68. It is noted, however, the at least one fixation aperture 70 and/or the at least one tool guide aperture 72 may extend outward a select distance from the surface of the talar PSI 68 via a respective channel 70A, 72A passing through a respective protrusion or guide 60B, 62B. For example, the protrusion or guide 70B, 72B may provide additional assistance in directing the drilling device and/or a pin to be positioned at the correct angle at the location on the surface of the talus 4, by providing a third dimension to direct (e.g., as opposed to an aperture 70, 72 providing only two dimensions to direct, or more specifically providing only location on the surface and not angle). Where the talar PSI 68 includes the protrusion or guide 70B, 72B, the protrusion or guide 70B, 72B may be fabricated as a single component with or integrated into the talar PSI 68. Alternatively, the protrusion or guide 70B, 72B may be separately fabricated and coupled to the talar PSI 68.

The talar PSI 68 includes at least one set of cutting guides 20. For example, the talar PSI 68 may include a first set of cutting guides 20 (e.g., for a horizontal cut), and a second set of cutting guides 20 (e.g., for a posterior cut). As the cutting guides 20 are a surface of the talar PSI 68, the talar PSI 68 may include one or more protection apertures 62 surrounding or flanking the at least one set of cutting guides 20.

It is noted the at least one fixation aperture 70, the at least one tool guide aperture 72 (and/or the channels 70A, 72A within the protrusions or guides 70B, 72B), and/or the at least one cutting guide 20 may be lined with or otherwise include a protective guide 21, as described throughout the present disclosure. The talar PSI 68 may include at least one guide aperture 64 for inserting the protective guide 21. It is noted, however, the talar PSI 68 may be fabricated to allow for the insertion of the protective guide 21 via the talar PSI interior surface 28 and/or the talar PSI exterior surface 34.

Where the protective guide 21 is inserted in the talar PSI 68 (and/or during fabrication of the talar PSI 68 in general), residual fabricating material powder and/or cleaning powder may need to be removed from the talar PSI 68. The talar PSI 68 may include at least one cleaning aperture 66 for removing the residual fabricating material powder and/or cleaning powder (e.g., during a manufacturing process). It is noted a guide aperture 64 and a cleaning aperture 66 may be the same aperture utilized for different functions at different stages of the fabrication and use cycle for the talar PSI 68.

The talar PSI 68 includes a handle 74 to adjust or manipulate the talar PSI 68 on the talus 4 to ensure proper position and direction of the drilling/reaming axis when aligning for drilling, cutting, and/or driving a pin. The handle may have a wavy shape to improve the grip with using it. The handle may be angled or aligned/straight to the main guiding direction. For example, the aligned handle may include a cavity to insert a stainless-steel cylinder. For instance, the stainless-steel cylinder may be self-locking, and/or may be perforated transversally to permit cleaning. By way of another example, the angled handle may include a smart connector that holds a stainless-steel cylinder to drill a metallic wire.

The handle may be attached to the talar PSI exterior surface 32. The handle may be fabricated via 3D printing, molding, casting, machining, or other additive manufacturing processes. For example, the handle may be fabricated as an attachment to the talar PSI exterior surface 32 or may be fabricated as a single component with the talar PSI exterior surface 32. It is noted the handle may be removable from the talar PSI exterior surface 32. For example, the handle may be cut or clipped by a wire cutter, sawed, broken at preformed break lines, uncoupled from an attachment point on the talar PSI exterior surface 32, or otherwise removed from the talar PSI exterior surface 32.

During surgery, the handle may be utilized to manually adjust or manipulate to the talar PSI 68 on the talus 4. To prevent slippage or other loss of control, the handle grip may be configured with improved tactile interfacing. For example, the handle grip may be contoured to conform to a particular user. In addition, the handle grip may be contoured to conform to a particular percentage or percentile of anthropometric data (e.g., ranging between the 5th and 95th percentile).

In one example embodiment, the handle grip may have a generally wavy shape. The wavy shape may be approximately sinusoidal and may include at least three peaks and two troughs. For example, the spacing between adjacent peaks may be configured for a particular user or may be approximated based on anthropometric data. The handle grip may be symmetric about a central axis defined through the length of the handle, with the peaks and troughs being generated concentric rings of increasing and decreasing diameter positioned along the length of the handle grip around the central axis. It is noted, however, the handle grip may not be symmetric, such that the wavy or contoured design may only be on one portion of the handle grip.

The handle may be angled with respect to the main guiding direction of the talar PSI 68. The angled handle may include a smart connector that houses a stainless-steel cylinder, through which a metallic wire may be drilled. The handle may be aligned or straight with respect to the main guiding direction of the talar PSI 68 on the talus 4. The aligned or straight handle may be self-locking, and/or may be perforated transversally to permit cleaning.

The angled handle may be beneficial where there is tight exposure. For example, preparing the talus 4 and/or the tibia 2 during arthroplasty usually involves approaching from a particular angle. Where there is difficult exposure, however, the surrounding bone structure, ligaments, and/or muscles may prevent the approach, and having an angled handle may allow the guide to be properly positioned without need. It is noted the embodiments directed to the angled versus aligned handles may be applicable to the alternate handle design without departing from the scope of the present disclosure, unless otherwise noted.

It is noted that where the talar PSI 68 includes protrusions or guides 62B, 70B, 72B, the protrusions or guides 62B, 70B, 72B may operate as a handle to hold and position the guide. Although not illustrated, it is contemplated any version of the talar PSI and/or any version of the tibial PSI as described in the various embodiments of the present disclosure may include a handle. In this regard, the above description should be regarded only as illustrative and should not be regarded as limiting.

The talar PSI 68 includes a block 76 representing a distal tibial resection. The block 76 may be usable for checking the adequation between planning and reality (e.g., transversal rotation, antero-posterior translation, or the like). For example, the block 76 may be in contact with the resected surface 54 of the tibia 2 when the talar PSI 68 is installed. By way of another example, the block 76 may include the talar PSI gap surface 34 and at least a portion of the talar PSI exterior surface 32. The block 76 may include a cavity 46.

It is noted any aperture positioned on or integrated in a tibial PSI as described throughout the present disclosure may be considered a "tibial aperture". In addition, it is noted any aperture positioned on or integrated in a talar PSI as described throughout the present disclosure may be considered a "talar aperture". Further, it is noted any "pin" as described throughout the present disclosure may be understood as being a "pin" or a "rod".

It is noted any discussion with respect to pre-defined angles and apertures may be understood as being dependent on a particular patient. For example, the structure of a tibia 2 and/or talus 4 of a first patient may require a first placement and/or arrangement of the various apertures described through the present disclosure with respect to tibial PSI and/or talar PSI. By way of another example, the structure of a tibia 2 and/or talus 4 of a second patient may require a second placement and/or arrangement of the various apertures described through the present disclosure with respect to tibial PSI and/or talar PSI, which may be different from the placement and/or arrangement for the first patient. In this regard, the tibial PSI and/or talar PSI may be fully customizable to the anatomy of a particular patient. It is noted, however, that select apertures may be universally placed on any tibial PSI and/or talar PSI, where it is determined the universal placement will not adversely interfere with the use of the tibial PSI and/or talar PSI for a patient (e.g., either with 100% certainty or within an acceptable statistical deviation from certainty (such as 95% percentile, or the like)).

In embodiments, one or more of the tibial PSI or the talar PSI as described throughout the present disclosure may include surfaces where markings may be printed or embedded. For example, the markings may be related to a manufacturing or distribution company (e.g., names, logos, or the like). By way of another example, the markings may be related to the patient (e.g., Patient ID, a barcode, quick response (QR) code, or other scannable device, or the like) to ensure there is no confusion in and/or swapping of components between pre-operative planning and intra-operative procedures, and/or to allow for intra-operative feedback (e.g., via an Augmented Reality (AR) application).

FIGS. 33-35 depict a flexible bone model (or flexion) 78, in accordance with embodiments of the present disclosure. The flexible bone model 78 may be generated based on the anatomy of a particular patient, and thus is fully customizable. It is noted, however, that select aspects of the flexible bone model 78 may be universal, where it is determined the universal placement will not adversely interfere with the use of the tibial PSI and/or the talar PSI for a patient (e.g., either with 100% certainty or within an acceptable statistical deviation from certainty (such as 95% percentile, or the like)).

The flexible bone model 78 may allow for testing the tibial PSI and/or the talar PSI of the PSI system during virtual pre-operative planning. The flexible bone model 78 may be manipulated to simulate the bone repositioning that will happen intra-operatively. For example, the flexible bone model 78 may include representative portions of a fibula 80, tibia 82, and/or talus 84. The tibia 82 and/or the talus 84 may include resected portions where the tibial PSI and/or the talar PSI may be inserted.

The flexible bone model 78 may include a range of articulation. For example, the flexible bone model 78 may allow for articulation ranging from 0 to 50 degrees from anatomic center of rotation. For instance, the flexible bone model 78 may allow for articulation ranging from 0 to 25 degrees. The flexible bone model 78 may include one or more mechanical actuators 86 to allow for and/or assist the articulation. For example, the mechanical actuators may include a spring, living hinge, plastic ring, or other component which may cause the flexible bone model 78 to adjust its angle of articulation and/or be held in place at a particular angle of articulation.

Advantages of the present disclosure include improved systems and methods for arthroplasty. In embodiments, the systems and method for arthroplasty include PSI which are mapped to a particular patient, such that observed abnormalities of the anatomy of the patient may be taken into consideration. In addition, the PSI of the present disclosure should allow for flexibility during arthroplasty, where additional or increased abnormalities of the anatomy of the patient are observed during the operation.

Although various embodiments of the present disclosure contemplate a PSI system with multiple PSI (e.g., including a tibial PSI, a talar PSI, and/or a connection guide), it is noted the PSI system may include only a single PSI which couples to the tibia or the talus separately, sequentially, or simultaneously. For example, the single PSI may only couple to the tibia or the talus, which is adjusted with assistance from the PSI relative to any bone not attached to a PSI. By way of another example, the single PSI may separately couple to both the tibia and the talus in a sequential order (and potentially in a different arrangement or configuration). For instance, the single PSI may be designed to have a first configuration which conforms to a tibia of a patient, and/or a second configuration which conforms to a talus of a patient. In addition, the single PSI may include a single configuration which may be universally placed on any tibia and/or talus, where it is determined the universal placement will not adversely interfere with the use for a patient (e.g., either with 100% certainty or within an acceptable statistical deviation from certainty (such as 95% percentile, or the like)). By way of another example, the single PSI may simultaneously couple to both the tibia and the talus. For instance, the single PSI may include adjustment mechanisms (e.g., threading, interlocking features, or the like) and/or may be configured to be moveable with the pins, which allow for the tibia and/or the talus to be moved relative to one another. In this regard, the embodiments throughout the present disclosure should be regarded only as illustrative and should not be regarded as limiting.

Although various embodiments of the present disclosure are contemplated for use with ankle arthroplasty in humans, no limitation with respect to the specific application, intended use, or procedure is provided. Indeed, it is contemplated that various inventive aspects of the present disclosure are capable for use with various operations, anatomical features, or the like without departing from the scope of the present disclosure. In this regard, the embodiments throughout the present disclosure should be regarded only as illustrative and should not be regarded as limiting.

Various features and embodiments of a PSI for arthroplasty have been provided herein. It will be recognized, however, that various features are not necessarily specific to certain embodiments and may be provided on any one or more embodiments. The present disclosure and embodiments provided herein are not mutually exclusive and may be combined, substituted, and omitted. The scope of the invention(s) provided herein is thus not limited to any particular embodiment, drawing, or particular arrangement of features.

While various embodiments of the present disclosure have been described in detail, it is apparent that modifications and alterations of those embodiments will occur to those skilled in the art. However, it is to be expressly understood that such modifications and alterations are within the scope and spirit of the present disclosure. Further, the invention(s) described herein are capable of other embodiments and of being practiced or of being carried out in various ways. In addition, it is to be understood that the phraseology and terminology used herein is for the purposes of description and should not be regarded as limiting.

What is claimed is:

1. A Patient-Specific Instrument (PSI) system for ankle arthroplasty, comprising:
   a tibial PSI with at least one tibial PSI interior surface contoured to conform to at least one tibial contact surface of a tibia, a contouring of the at least one tibial PSI interior surface being operable to provide an indication of a mispositioning of the tibial PSI on the tibia, the tibial PSI including at least one tibial aperture defined by a first channel within a first protrusion that extends outward from a tibial PSI exterior surface and that is operable to receive at least a first pin, the at least one tibial aperture corresponding to a pre-determined placement of the at least a first pin within the tibia, wherein the tibial PSI is couplable to the tibia via the at least a first pin; and
   a talar PSI with at least one talar PSI interior surface contoured to conform to at least one talar contact surface of a talus, a contouring of the at least one talar PSI interior surface being operable to provide an indication of a mispositioning of the talar PSI on the talus, the talar PSI including at least one talar aperture defined by a second channel within a second protrusion that extends outward from a talar PSI exterior surface and that is operable to receive at least a second pin, the at least one talar aperture corresponding to a pre-determined placement of the at least a second pin within the talus, wherein the talar PSI is couplable to the talus via the at least a second pin, wherein the tibial PSI includes at least one cutting guide positioned at a distal end of the tibial PSI and operable to receive a cutting device for producing at least one resected surface on the tibia, and at least one additional contact coupled to the at least one cutting guide by at least one connector, wherein the at least one additional contact is operable to provide an additional indication of the mispositioning of the tibial PSI and is operable as an additional substantially parallel cutting guide, wherein the at least one additional contact is removable from the at least one cutting guide during production of the at least one resected surface on the tibia, wherein the talar PSI exterior surface is operable to be aligned with an exterior surface of the tibia, and wherein the talus includes a talar PSI gap surface operable to be aligned with the at least one resected surface of the tibia.

2. The PSI system of claim 1, wherein at least one of the pre-determined placement of the at least a first pin within the tibia or the pre-determined placement of the at least a second pin within the talus is pre-determined during at least one virtual pre-operative planning.

3. The PSI system of claim 2, wherein at least one of:
the tibial PSI is designed from a scan of the tibia during the at least one virtual pre-operative planning; or
the talar PSI is designed from a scan of the talus during the at least one virtual pre-operative planning.

4. The PSI system of claim 1, further comprising:
a connection guide configured to align at least one of the tibia or the talus during intra-operative procedures, wherein the connection guide includes a plurality of guide apertures, and wherein the connection guide is operable to at least one of:
receive the at least a first pin coupling the tibial PSI to the tibia within a first guide aperture of the plurality of guide apertures, where the at least a first pin is positioned within the tibia via the pre-determined placement of the at least one tibial aperture; or
receive the at least a second pin coupling the talar PSI to the talus within a second guide aperture of the plurality of guide apertures, where the at least a second pin is positioned within the talus via the pre-determined placement of the at least one talar aperture.

5. The PSI system of claim 4, wherein at least one of the tibial PSI, the talar PSI, or the connection guide is fabricated via at least one additive manufacturing process.

6. The PSI system of claim 1, wherein the at least a first pin includes at least one distal pin and at least one proximal pin, wherein the at least one tibial aperture includes at least one distal drilling aperture defined by a second channel of the tibial PSI and corresponding to a pre-determined placement of the at least one distil pin within the tibia and at least one proximal drilling aperture defined by the first channel of the tibial PSI and corresponding to a pre-determined placement of the at least one proximal pin within the tibia.

7. The PSI system of claim 1, wherein the at least a second pin includes at least one alignment pin, wherein the at least one talar aperture includes at least one alignment aperture corresponding to a pre-determined placement of the at least one alignment pin within the talus.

* * * * *